United States Patent
Klosin et al.

(10) Patent No.: US 6,555,634 B1
(45) Date of Patent: Apr. 29, 2003

(54) DI- AND TRI-HETEROATOM SUBSTITUTED INDENYL METAL COMPLEXES

(75) Inventors: Jerzy Klosin, Midland, MI (US); William J. Kruper, Jr., Sanford, MI (US); Peter N. Nickias, Midland, MI (US); Jasson T. Patton, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/936,018

(22) PCT Filed: Mar. 17, 2000

(86) PCT No.: PCT/US00/07372

§ 371 (c)(1),
(2), (4) Date: Sep. 7, 2001

(87) PCT Pub. No.: WO00/69871

PCT Pub. Date: Nov. 23, 2000

Related U.S. Application Data

(60) Provisional application No. 60/133,994, filed on May 13, 1999.

(51) Int. Cl.$^7$ .................................................. C08F 4/64
(52) U.S. Cl. ........................ 526/161; 526/160; 526/170; 526/172; 556/11; 556/51; 556/52; 502/103
(58) Field of Search .................. 526/161, 172, 526/160, 170, 126; 556/51, 52, 11; 502/103

(56) References Cited

U.S. PATENT DOCUMENTS

| | | | |
|---|---|---|---|
| 5,055,438 A | 10/1991 | Canich | 502/117 |
| 5,057,475 A | 10/1991 | Canich et al. | 502/104 |
| 5,064,802 A | 11/1991 | Stevens et al. | 502/155 |
| 5,096,867 A | 3/1992 | Canich | 502/103 |
| 5,132,380 A | 7/1992 | Stevens et al. | 526/126 |
| 5,304,614 A | 4/1994 | Winter et al. | 526/127 |
| 5,321,106 A | 6/1994 | LaPointe | 526/126 |
| 5,350,817 A | 9/1994 | Winter et al. | 526/119 |
| 5,374,696 A | 12/1994 | Rosen et al. | 526/126 |
| 5,470,993 A | 11/1995 | Devore et al. | 556/11 |
| 5,621,126 A | 4/1997 | Canich et al. | 556/9 |
| 5,703,187 A | 12/1997 | Timmers | 526/282 |
| 5,721,185 A | 2/1998 | LaPointe et al. | 502/117 |
| 6,015,868 A * | 1/2000 | Nickias et al. | 526/127 |
| 6,268,444 B1 * | 7/2001 | Klosin et al. | 526/127 |

FOREIGN PATENT DOCUMENTS

| | | |
|---|---|---|
| EP | 416815 | 3/1991 |
| EP | 514828 | 11/1992 |
| EP | 582195 | 2/1994 |
| EP | 577581 | 11/1994 |
| WO | WO 95/07942 | 3/1995 |
| WO | WO 96/13529 | 5/1996 |
| WO | WO 98/06727 | 2/1998 |
| WO | WO 98/06728 | 2/1998 |
| WO | WO 00/69870 A1 * | 11/2000 ........... C08F/17/00 |

OTHER PUBLICATIONS

J. Organometallic Chem. 1996, 520, 63–68 E. Barsties, S. Schaible, M. H. Prosenc, u. Rief, W. Roll, O. Weyland, B. Dorerer, and H. H. Brintzinger.

J. Organometallic Chem. 1996, 519, 269–272, H. Plenio, and D. Birth.

* cited by examiner

*Primary Examiner*—David W. Wu
*Assistant Examiner*—Rip A. Lee

(57) ABSTRACT

Novel metal complexes containing at least two heteroatoms attached to an indenyl or substituted indenyl radical which is bridged by ligand group thereby forming a covalent or coordinate/covalent bond to the metal, the use of such metal complexes in the formation of polymerization catalysts and processes for polymerizing α-olefins using such catalysts.

8 Claims, No Drawings

DI- AND TRI-HETEROATOM SUBSTITUTED INDENYL METAL COMPLEXES

This application claims the benefit of Provisional Application No. 60/133,994 filed May 13, 1999.

FIELD OF THE INVENTION

This invention relates to a class of metal complexes, the ligands used to prepare these metal complexes and to olefin polymerization catalysts derived therefrom that are particularly suitable for use in a polymerization process for preparing polymers by polymerization of α-olefins and mixtures of α-olefins.

BACKGROUND

Constrained geometry metal complexes and methods for their preparation are disclosed in U.S. Pat. No. 5,703,187; U.S. Pat. No. 5,321,106; U.S. Pat. No. 5,721,185; U.S. Pat. No. 5,374,696; U.S. Pat. No. 5,055,438; U.S. Pat. No. 5,057,475; U.S. Pat. No. 5,096,867; U.S. Pat. No. 5,064,802; U.S. Pat. No. 5,132,380; U.S. Pat. No. 5,470,993, as well as EP-A-514,828, and elsewhere.

U.S. Pat. Nos. 5,350,817 and 5,304,614 disclose bridged zirconocene complexes, wherein two indenyl groups are covalently linked together by a bridge containing carbon or silicon, which are useful for the polymerization of propylene.

EP-A-577,581 discloses unsymmetrical bis-Cp metallocenes containing a fluorenyl ligand with heteroatom substituents.

E. Barsties; S. Schaible; M.-H. Prosenc; U. Rief; W. Roll; O. Weyland; B. Dorerer; H.-H. Brintzinger *J. Organometallic Chem.* 1996, 520, 63–68, and H. Plenio; D. Birth *J. Organometallic Chem.* 1996, 519, 269–272 disclose systems in which the cyclopentadienyl ring of the indenyl is substituted with a dimethylamino group in non-bridged and Si-bridged bis-indenyl complexes useful for the formation of isotactic polypropylene and polyethylene.

Disclosure of random heteroatom substitution in mono-Cp metallocenes is found in EP-A-416,815, WO 95/07942, WO 96/13529, and U.S. Pat. No. 5,096,867 and U.S. Pat. No. 5,621,126. Specific heteroatom substitution of the 3- and 2-position of indenyl complexes of group 4 metals was disclosed in WO98/06727 and WO/98/06728 respectively. The foregoing specifically substituted metal complexes have produced improved catalyst results, however, problems still remain with catalyst efficiency and deactivation of the catalyst under high temperature polymerization conditions. It would be advantageous to be able to produce polyolefins with higher molecular weights. It would also be advantageous to be able to improve other physical characteristics of the polymers produced by altering the substitution around the cyclopentadienyl group of the metallocene complexes used in olefin polymerization catalyst systems.

SUMMARY OF THE INVENTION

According to the present invention there are provided metal complexes corresponding to the formula:

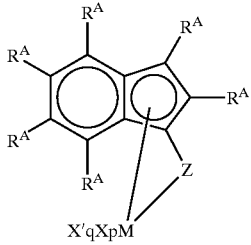

I where M is a metal from one of Groups 3 to 13 of the Periodic Table of the Elements, the lanthanides or actinides, which is in the +2, +3 or +4 formal oxidation state, $R^A$ independently each occurrence is hydrogen, $R^B$ or $TR^B{}_j$, with the proviso that in at least two but not more than three occurrences $R^A$ is $TR^B{}_j$, j is 1 or 2, and when j is 1, T is oxygen or sulfur and when j is 2, T is nitrogen or phosphorus, $R^B$ independently each occurrence is a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, or two $R^B$ groups are joined together forming a divalent ligand group;

Z is a divalent moiety bound to the substituted indenyl group and bound to M by either covalent or coordinate/covalent bonds, comprising boron or a member of Group 14 of the Periodic Table of the Elements, and also comprising nitrogen, phosphorus, sulfur or oxygen;

X is an anionic or dianionic ligand group having up to 60 atoms (including ligands that are cyclic, delocalized, π-bound ligand groups);

X' independently each occurrence is a Lewis base ligand having up to 20 atoms;

p is a number from 0 to 5, (when each X is an anionic ligand, p is two less than the formal oxidation state of M, when some or all X groups are dianionic ligand groups each dianionic X group accounts for two valencies and p is correspondingly reduced in value); and q is zero, 1 or 2.

Certain of the metal complexes wherein the metal is a Group 3 or lanthanide metal are catalytically active for polymerization of olefins without addition of an activator or cocatalyst. Preferably however a cocatalyst is present. Accordingly, in one embodiment according to the present invention, there is provided a catalyst composition for olefin polymerization comprising:

(A) a catalyst component comprising a metal complex as previously defined; and (B) a cocatalyst component comprising an activating cocatalyst wherein the molar ratio of (A) to (B) is from 1:10,000 to 100:1; or optionally catalyst component (A) is activated by use of an activating technique.

Another embodiment of this invention is a catalyst composition for olefin polymerization comprising:

(A) a catalyst component comprising a metal complex as previously defined; and (B) a cocatalyst component comprising an activating cocatalyst wherein the molar ratio of (A) to (B) is from 1:10,000 to 100:1 wherein the metal complex is in the form of a radical cation.

Further according to the present invention there is provided a process for the polymerization of olefins comprising contacting one or more $C_{2-20}$ α-olefins under polymerization conditions with one of the aforementioned catalyst compositions.

A preferred process of this invention is a high temperature solution polymerization process for the polymerization of olefins comprising contacting one or more $C_{2-20}$ α-olefins under polymerization conditions with one of the aforementioned catalyst compositions at a temperature from 100° C. to 250° C.

Within the scope of this invention are the polyolefin products produced by the aforementioned processes. Preferred products have long chain branching and/or reverse molecular architecture.

This invention also provides a cyclopentadienyl-containing ligand of one of the aforementioned metal complexes where the ligand is in the form of:

(A) a free acid with 2 protons capable of being deprotonated;

(B) a dilithium, disodium or dipotassium salt;

(C) a magnesium salt: or (D) a mono or disilylated dianion.

Within the scope of this aspect of the invention is the use of one of these ligands for synthesis to produce a metal complex of this invention, or, more specifically, the use of one of these ligands for synthesis to produce a metal complex comprising a metal from one of Groups 3 to 13 of the Periodic Table of the Elements, the lanthanides or actinides, and from 1 to 4 of the ligands.

The present catalysts and processes result in the highly efficient production of high molecular weight olefin polymers over a wide range of polymerization conditions, and especially at elevated temperatures. They are especially useful for the solution or bulk polymerization of ethylene/propylene (EP polymers), ethylene/octene (EO polymers), ethylene/styrene (ES polymers), propylene and ethylene/propylene/diene (EPDM polymers) wherein the diene is ethylidenenorbornene, 1,4-hexadiene or similar nonconjugated diene. The use of elevated temperatures dramatically increases the productivity of such processes due to the fact that increased polymer solubility at elevated temperatures allows the use of increased conversions (higher concentration of polymer product) without exceeding solution viscosity limitations of the polymerization equipment. In addition, the use of higher polymerization temperatures results in a reduction of energy costs needed to devolatilize the reaction product.

The catalysts of this invention may also be supported on a support material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

DETAILED DESCRIPTION

All references to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups. The full teachings of any patent, patent application, provisional application, or publication referred to herein are hereby incorporated by reference. The term "reverse molecular architecture" as used herein refers to a copolymer of two or more olefins wherein higher molecular weight fractions of the polymer contain increased content of the higher molecular weight comonomer.

Olefins as used herein are $C_{2-20}$ aliphatic or aromatic compounds containing vinylic unsaturation, as well as cyclic compounds such as cyclobutene, cyclopentene, and norbornene, including norbornene substituted in the 5- and 6-positions with $C_{1-20}$ hydrocarbyl groups. Also included are mixtures of such olefins as well as mixtures of such olefins with $C_{4-40}$ diolefin compounds. Examples of the latter compounds include ethylidene norbornene, 1,4-hexadiene, norbornadiene, and the like. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a nonconjugated diene, such as, for example, EPDM terpolymers.

Preferred coordination complexes according to the present invention are complexes corresponding to the formulas:

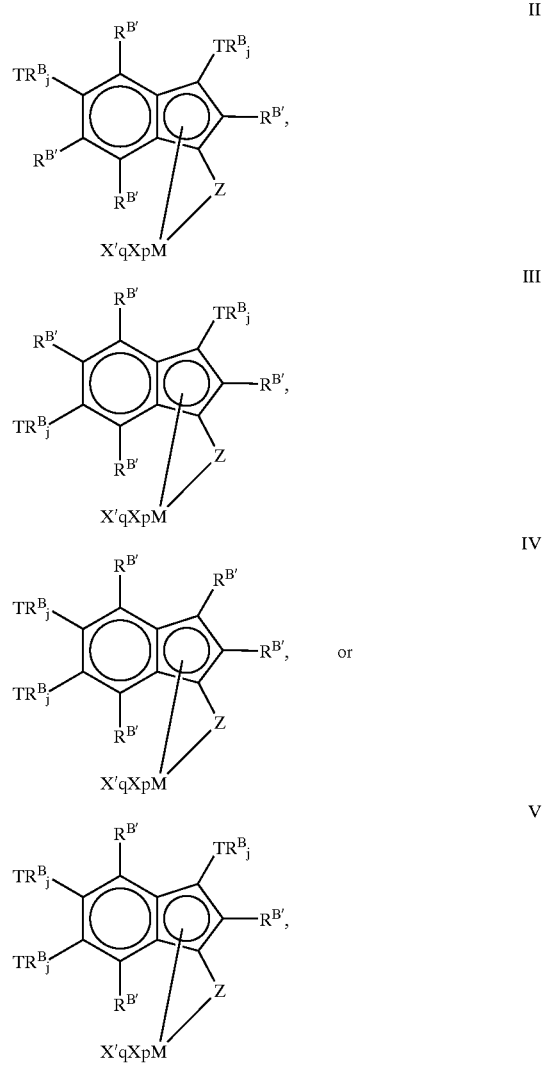

where T, $R^B$, j, M, Z, X, X', p and q are as previously defined, and $R^{B'}$ independently is hydrogen or a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, or two $R^{B'}$ groups are joined together forming a divalent ligand group.

Preferred $R^B$ and $R^{B'}$ groups are hydrogen and hydrocarbyl, hydrocarbylsilyl, hydrocarbyloxy-substituted hydrocarbyl, hydrocarbylamino-substituted hydrocarbyl and halogen substituted hydrocarbyl groups having from 1 to 20 nonhydrogen atoms, more preferably hydrogen, alkyl, aryl or aralkyl.

More preferred $R^B$ groups are hydrogen, hydrocarbyl, hydrocarbylsilyl, hydrocarbyloxy-substituted hydrocarbyl, hydrocarbylamino-substituted hydrocarbyl having from 1 to 20 nonhydrogen atoms, most preferably hydrogen, alkyl, aryl or aralkyl, or two $R^B$ groups together are an alkylene group having from 1 to 20 carbons.

Preferred T groups are O or N, more preferably N.

Preferred heteroatom-containing substituents are at the 3, 5, or 6-position of the substituted indenyl group and are those wherein the $TR^B_j$ group is methoxy, ethoxy, propoxy, methylethyloxy, 1,1-dimethyethyloxy, trimethylsiloxy, 1,1-dimethylethyl(dimethylsilyl)oxy, dimethylamino, diethylamino, methylethylamino, methylphenylamino, dipropylamino, dibutylamino, piperidino, morpholino, pyrrolidino, hexahydro-1H-azepin-1-yl, hexahydro-1(2H)-azocinyl, octahydro-1H-azonin-1-yl or octahydro-1(2H)-azecinyl, or two adjacent $TR^B_j$ groups are —OCH$_2$O—. More preferred are those wherein the $TR^B_j$ group is dimethylamino, methylphenylamino, piperidino or pyrrolidino.

Preferred X groups are halide, alkyl, cycloalkyl, aryl, aralkyl or cycloalkadienyl groups, said X having from 1 to 20 atoms other than hydrogen.

Preferred X' groups are carbon monoxide; phosphines, especially trimethylphosphine, triethylphosphine, triphenylphosphine and bis(1,2-dimethylphosphino)ethane; $P(OR^i)_3$, wherein $R^i$ is hydrocarbyl, silyl or a combination thereof; ethers, especially tetrahydrofuran; amines, especially pyridine, bipyridine, tetramethylethylenediamine (TMEDA), and triethylamine; olefins; and conjugated dienes having from 4 to 40 carbon atoms. Complexes including the latter X' groups include those wherein the metal is in the +2 formal oxidation state.

In another aspect of this invention either the ligand or metal complex has one or more fused rings or ring systems in addition to the Cp or indenyl wherein the one or more fused rings or ring systems contain two or more ring heteroatoms which are N, O, S, or P. Preferred ring heteroatoms are N or O, with N being more highly preferred.

The preferred complexes include ones corresponding to the formulas:

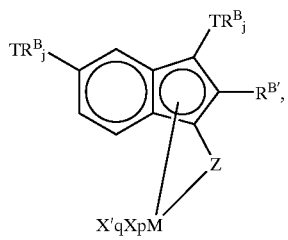

VI

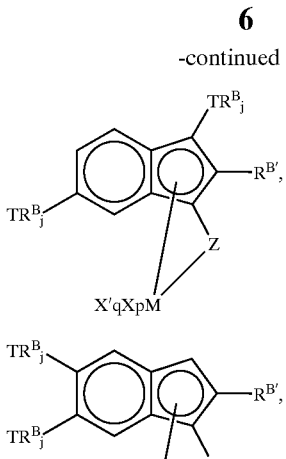

VII

VIII or

IX where Z, T, $R^B$, $R^{B'}$, j, M, X, X', p and q are as previously defined with respect to formulas II, III IV and V.

Highly preferred are the metal complexes, the heteroatom-containing ligands thereof, and metallated derivatives thereof, where —Z— is —(Z*—Y)—, with Z* bonded to Cp and Y bonded to M, and Y is —O—, —S—, —NR*—, —NR*$_2$, —PR*, —PR*$_2$, —OR*, or —SR*;

Z* is SiR*$_2$, CR*$_2$, SiR*$_2$SiR*$_2$, CR*$_2$CR*$_2$, CR*=CR*, CR*$_2$SiR*$_2$, CR*$_2$SiR*$_2$CR*$_2$, SiR*$_2$CR*$_2$SiR*$_2$, CR*$_2$CR*$_2$SiR*$_2$, CR*$_2$CR*$_2$CR*$_2$, or GeR*$_2$; and R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms, and optionally, two R* groups from Z, or an R* group from Z and an R* group from Y form a ring system;

when p is 2, q is zero, M is in the +3 or +4 formal oxidation state, and X is independently each occurrence chloride, methyl, benzyl, trimethylsilylmethyl, allyl, cyclopentadienyl, pyrrolyl or two X groups together are 1,4-butane-diyl, 2-butene-1,4-diyl, 2,3-dimethyl-2-butene-1,4-diyl, 2-methyl-2-butene-1,4-diyl, or xylanediyl.

Also highly preferred are the metal complexes, the heteroatom-containing ligands thereof, and metallated derivatives thereof, where —Z— is —Z*—Y—, with Z* bonded to Cp and Y bonded to M, and Y is —O—, —S—, —NR*—, or —PR*—;

Z* is SiR*$_2$, CR*$_2$, SiR*$_2$SiR*$_2$, CR*$_2$CR*$_2$, CR*=CR*, CR*$_2$SiR*$_2$, CR*$_2$SiR*$_2$CR*$_2$, SiR*$_2$CR*$_2$SiR*$_2$, CR*$_2$CR*$_2$SiR*$_2$, CR*$_2$CR*$_2$CR*$_2$, or GeR*$_2$; and R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms, and optionally, two R* groups from Z, or an R* group from Z and an R* group from Y form a ring system;

where p is 1, q is zero, M is in the +2 or +3 formal oxidation state, and X is 2-(N,N-dimethyl)aminobenzyl, 2-(N,N-dimethylaminomethyl)phenyl, allyl, methallyl, trimethylsilylallyl, or cyclopentadienyl.

Also highly preferred are the metal complexes, the heteroatom-containing ligands thereof, and metallated derivatives thereof, where —Z— is —(Z*—Y)—, with Z* bonded to Cp and Y bonded to M, and Y is —O—, —S—, —NR*—, or —PR*—;

Z* is SiR*$_2$, CR*$_2$, SiR*$_2$SiR*$_2$, CR*$_2$CR*$_2$, CR*=CR*, CR*$_2$SiR*$_2$, CR*$_2$SiR*$_2$CR*$_2$, SiR*$_2$CR*$_2$SiR*$_2$, CR*$_2$CR*$_2$SiR*$_2$, CR*$_2$CR*$_2$CR*$_2$, or GeR*$_2$; and R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms, and optionally, two R* groups from Z, or an R* group from Z and an R* group from Y form a ring system;

when p is 0, q is 1, M is in the +2 formal oxidation state, and X' is 1,4-diphenyl-1,3-butadiene, 1,3-pentadiene or 2,4-hexadiene.

A variety of metals can be used in the preparation of the metal complexes of this invention. Desirably M is a metal from one of Groups 3 to 13 of the Periodic Table of the Elements, the lanthanides or actinides, which is in the +2, +3 or +4 formal oxidation state, more desirably M is a metal from one of Groups 3 to 13. Most preferred are those where M is a metal from Group 4. Titanium is the most highly preferred metal.

Further preferred coordination complexes of the invention are complexes corresponding to the formulas:

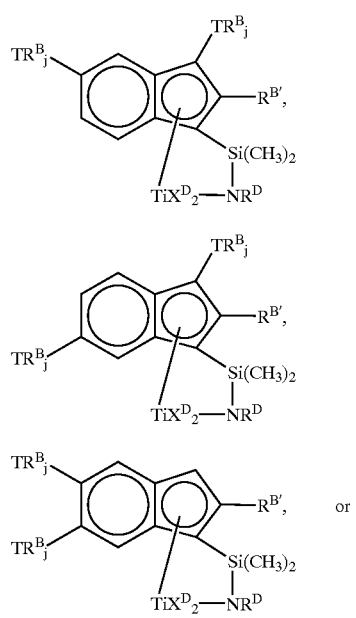

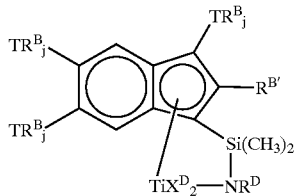

wherein, TR$^B_j$ is dimethylamino, pyrrolidino, or methoxy, or two adjacent TR$^B_j$ groups together are —OCH$_2$O—; X$^D$ independently each occurrence is chloride or methyl or two X$^D$ groups collectively are a neutral 2,4-hexadiene or 1,4-diphenyl-butadiene group, and R$^D$ is t-butyl, isopropyl or cyclohexyl. Particularly preferred complexes are those of the foregoing formulas X, XI, XII, and XIII, wherein R$^{B'}$ is hydrogen or methyl, TR$^B_j$ is dimethylamino and pyrrolidino and X$^D$ is halogen or methyl.

The complexes can be prepared by use of well-known synthetic techniques. Optionally a reducing agent can be employed to produce the lower oxidation state complexes. Such a process is disclosed in U.S. Pat. No. 5,470,993. The reactions are conducted in a suitable noninterfering solvent at a temperature from −100 to 300° C., preferably from −78 to 100° C., most preferably from 0 to 50° C. By the term "reducing agent" herein is meant a metal or compound which, under reducing conditions, causes the metal M to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium or magnesium metal and n-butyllithium.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, C$_{1-4}$ dialkyl ethers, C$_{1-4}$ dialkyl ether derivatives of (poly)alkylene glycols, and tetrahydrofuran. Mixtures of the foregoing are also suitable.

The substituted inden-1-yl containing compounds may be prepared by condensation of ketones with an amine or alcohol using standard synthetic techniques. Condensation with amines is well known from the teachings of W. E. Noland, V. Kameswaran *J. Org. Chem.* 1981, 46, 1940–1944, and elsewhere. An acid catalyst such as p-toluene sulfonic acid may be employed, and the water by-product is desirably azeotropically removed using a benzene or toluene solvent under reflux conditions. A similar technique has been disclosed in O. Cervinka, *The Chemistry of Enamines*, Part 1, Ch. 9; Z. Rappoport, Ed.; Wiley Interscience, New York, 1994, 468–500. With more sterically-hindered ketones or more volatile amines, such as dimethyl amine, it may be preferable to employ stronger dehydrating reagents such as titanium chloroamides, which may be generated in situ from titanium tetrachloride and the condensation amine. This technique has been previously disclosed in R. Carlson, A. Nilsson, *Acta Chemica Scandinavica*, B 38, 1984, 49–53.

Subsequent formation of the substituted ligand groups and ultimately the metal complexes themselves uses conventional organometallic synthetic procedures. Neutral amino-substituted indenes may be prepared directly by contacting a ketone with titanium tetraamide in an inert diluent at a temperature from 25 to 150° C.

Desirably, the substituted indenes and intermediates prepared according to the invention are highly pure and free of ketone starting reactants, Aldol by-products, and higher weight reaction products which typically accompany product formation. Desirably the intermediate products may be subjected to purification procedures such as chromatographic purification, distillation, recrystallization, or other suitable technique to produce the desired purity in the final product. Rapid distillation of polyamine compounds is preferred to prevent thermal polymerization at elevated temperatures.

Conversion of the substituted indenyl ligand to its corresponding anionic salt may be accomplished by reaction with an appropriate base of suitable strength in an appropriate noninterfering solvent. Under anaerobic, anhydrous conditions, the salt may be filtered, washed and dried in nearly quantitative yield.

The formation of ligands containing the —Z— functional group from the substituted indene metal compounds may be accomplished by reaction with an electrophile such as a halogenated secondary alkylamine or halogenated secondary silylamine to give the corresponding alkylamine or silylamine substituted compound. Suitable halogenated secondary alkylamines or halogenated secondary silylamines include (t-butyl)(chlorodimethylsilyl)amine, (t-butyl) (chlorodimethylsilylmethyl)amine, (t-butyl) (bromomethyidimethylsilyl)amine, (t-butyl)(2-chloroethyl) amine, (chlorodimethylsilyl)(phenyl)amine, (adamantyl) (chlorodiphenyisilyl)amine, (chlorodimethylsilyl) (cyclohexyl)amine, (benzyl)(chlorodimethylsilyl)amine and (t-butyl)(chloromethylphenylsilyl)amine. The technique is based upon the anion alkylation method previously disclosed by WO 93/08199 and *Organometallics*, 1996, 15(6), 1572–81. In a preferred embodiment, the lithio derivative of the anionic salt is slowly added to a molar excess of (t-butyl)(chlorodimethylsilyl)amine in an ether solvent. This ligand may also be converted to its insoluble anionic salt by reaction of the free base with two equivalents of a base of suitable strength in an appropriate noninterfering solvent.

By the term "appropriate noninterfering solvent" is meant a solvent that doesn't interfere with the formation of, or react deleteriously with, the desired product. Such solvents suitable for the preparation of the anionic salts of the invention include, but are not limited to aliphatic and aromatic hydrocarbons, particularly straight and branched chain hydrocarbons such as butane, pentane, hexane, heptane, octane, decane, including their branched isomers and mixtures thereof; cyclic and alicyclic hydrocarbons such as cyclohexane, cycloheptane, methylcyclohexane, methylcycloheptane and mixtures thereof; aromatic and hydrocarbyl-substituted aromatic compounds such as benzene, toluene, xylene, ethylbenzene, diethylbenzene and mixtures thereof; ethers and cyclic ethers, particularly $C_{1-6}$ dialkyl ethers, such as diethyl ether, dibutyl ether and methyl-t-butyl ether, $C_{1-6}$ dialkyl ether derivatives of (poly)alkylene glycols, such as dimethoxyethane, and dioxane and THF and mixtures thereof. Mixtures of the foregoing are also suitable.

Bases of suitable strength for the preparation of the dianionic salts of the invention include hydrocarbyl salts of Group 1 and Group 2 metals, especially alkyl or aryl salts of lithium or magnesium, such as methyllithium, ethyllithium, n-butyllithium, s-butyllithium, t-butyllithium, phenyllithium, methyl magnesium chloride, ethyl magnesium bromide, i-propyl magnesium chloride, dibutylmagnesium, (butyl)(ethyl)magnesium, dihexylmagnesium; Group 1 or Group 2 metals, such as lithium, sodium, potassium and magnesium; Group 1, Group 2 or Group 13 metal hydrides, such as lithium hydride, sodium hydride, potassium hydride or lithium aluminum hydride; Group 1 or Group 2 metal amide complexes, such as lithium diisopropylamide, lithium dimethylamide, lithium hexamethyidisilazide, sodamide and magnesium diisopropylamide.

Bases of suitable strength for the preparation of the anionic salts of the invention include the foregoing as well as Group 1 or Group 2 metal alkoxide complexes, such as sodium ethoxide, sodium t-butoxide, potassium butoxide and potassium amylate.

The metallation of the dianionic salt may be accomplished by methods cited in this art as well. Reaction of the dianionic salt with $TiCl_3.(THF)_3$, followed by oxidation with methylene chloride or lead dichloride, substantially according to the technique of *Chem. Ber.*, 1996, 129, 1429–1431 or EP-A-514,828 affords the titanium (IV) dichloride complex in very high yield. The dichloride may thereafter be silylated or hydrocarbylated by ligand exchange with an appropriate silylating or hydrocarbylating agent, such as methyllithium, methyl magnesium chloride, benzyl potassium, allyl lithium, trimethylsilylmethyl lithium, neopentyl magnesium bromide and phenyllithium.

A general method for producing the titannium(II) diene complex from the corresponding titanium(IV) dichloride preferably involves the treatment of the dichloride with n-butyl lithium in the presence of an appropriate diene. A similar technique has been described in *Organometallics*, 1995, 14, 3132–3134 as well as in U.S. Pat. No. 5,556,928.

The formation of the metal complexes wherein the metal is in the +3 formal oxidation state according to the invention can be accomplished by any of several synthesis methods. One technique involves the reaction under anaerobic and anhydrous conditions of the dianionic salts with trivalent metal salts, such as Group 4 metal (III) halide or alkoxide complexes, optionally followed by silylation or hydrocarbylation with suitable silylating or hydrocarbylating agents, to form the corresponding halide, alkoxide, silyl or hydrocarbyl complexes of the invention. A further synthesis method involves reducing an appropriate metal (IV) complex with a suitable reducing agent to the corresponding metal (III) complex. Suitable reducing agents especially include zinc, aluminum, lithium, and magnesium.

Suitable silylating and hydrocarbylating agents for the metal complexes of the invention include the corresponding silyl or hydrocarbyl derivatives of Group 1, 2 or 13 metals or Group 2 metal halides, preferably lithium sodium, potassium, magnesium and aluminum, or Group 2 metal Grignards. Examples of suitable hydrocarbyl and silyl groups include alkyl, such as methyl, ethyl, propyl, butyl, neopentyl and hexyl; aryl, such as phenyl, naphthyl and biphenyl; aralkyl, such as benzyl, tolylmethyl, diphenylmethyl; alkaryl, such as tolyl and xylyl; allyl; silyl- or alkyl-substituted allyl, such as methylallyl, trimethylsilylallyl, dimethylallyl and trimethylallyl; trialkylsilyl, such as trimethylsilyl and triethylsilyl; trialkylsilylalkyl, such as trimethylsilylmethyl; pentadienyl; alkyl- or silyl-substituted pentadienyl, such as methylpentadienyl, dimethylpentadienyl, trimethylsilylpentadienyl, bis (trimethylsilyl)pentadienyl, cyclohexadienyl and dimethyicyclohexadienyl; dialkylaminoalkaryl, such as o-(N,N- dimethylaminomethyl)phenyl; and dialkylaminoaralkyl, such as o-(N,N-dimethylamino)benzyl. Preferred silylating and hydrocarbylating agents include trimethylaluminum, methyllithium, methylmagnesiumchloride, neopentyllithium, trimethylsilylmethylmagnesiumchloride and phenyllithium. Stabilizing group-containing hydrocarbylating agents are also included, especially the stabilizing group-containing hydrocarbylating agents and salts of the stabilizing group-containing hydrocarbyl groups described in U.S. Pat. No. 5,504,224, whose salts include, for example, benzyl potassium, 2-(N,N-dimethylamino)benzyllithium, allyllithium and dimethylpentadienyl potassium. Such stabilizing groups are further described in U.S. Pat. No. 5,374,696, and elsewhere.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum-modified methylalumoxane, or isobutylalumoxane; neutral Lewis acids, such as $C_{3-45}$ hydrocarbyl substituted Group 13 compounds, especially tri(hydrocarbyl)aluminum- or tri(hydrocarbyl)boron-compounds and halogenated (including perhalogenated) derivatives thereof, having from 1 to 15 carbons in each hydrocarbyl or halogenated hydrocarbyl group, more especially perfluorinated tri(aryl)boron compounds, and most especially tris(o-nonafluorobiphenyl) borane, tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in EP-A-277,003 and U.S. Pat. No. 5,153,157, U.S. Pat. No. 5,064,802, U.S. Pat. No. 5,321,106, and U.S. Pat. No. 5,721,185.

Combinations of neutral Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane, tris(o-nonafluorobiphenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. A benefit according to the present invention is the discovery that the most efficient catalyst activation using such a combination of tris(pentafluorophenyl)borane/alumoxane mixture occurs at reduced levels of alumoxane. Preferred molar ratios of metal complex:tris(pentafluorophenyl)borane:alumoxane are from 1:1:1 to 1:5:5, more preferably from 1:1:1.5 to 1:5:3. The surprising efficient use of lower levels of alumoxane with the present invention allows for the production of olefin polymers with high catalytic efficiencies using less of the expensive alumoxane cocatalyst. Additionally, polymers with lower levels of aluminum residue, and hence greater clarity, are obtained.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the metal complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

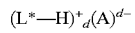

wherein:

L* is a neutral Lewis base;

(L*—H)⁺ is a Bronsted acid;

(A)$^{d-}$ is a noncoordinating, compatible anion having a charge of d−, and d is an integer from 1 to 3.

More preferably (A)$^{d-}$ corresponds to the formula: [M'Q₄]⁻;

wherein:

M' is boron or aluminum in the +3 formal oxidation state; and

Q independently each occurrence is selected from hydride, dialkylamido, halide, hydrocarbyl, hydrocarbyloxide, halosubstituted-hydrocarbyl, halo-substituted hydrocarbyloxy, and halo-substituted silyl-hydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counterion has a single negative charge and is A⁻. Activating cocatalysts comprising boron which are particularly useful in the preparation of catalysts of this invention may be represented by the following general formula:

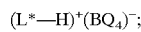

wherein:

L* is as previously defined;

B is boron in a formal oxidation state of 3; and

Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Most preferably, Q is each occurrence a fluorinated aryl group, especially, a pentafluorophenyl group.

Illustrative, but not limiting, examples of ion forming compounds comprising proton donatable cations which may be used as activating cocatalysts in the preparation of the catalysts of this invention are tri-substituted ammonium salts such as:

trimethylammonium tetraphenylborate,
methyldioctadecylammonium tetraphenylborate,
triethylammonium tetraphenylborate,
tripropylammonium tetraphenylborate,
tri(n-butyl)ammonium tetraphenylborate,
methyltetradecyloctadecylammonium tetraphenylborate,
N,N-dimethylanilinium tetraphenylborate,
N,N-diethylanilinium tetraphenylborate,
N,N-dimethyl(2,4,6-trimethylanilinium) tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl(2,4,6-trimethylanilinium) tetrakis(pentafluorophenyl)borate,
trimethylammonium tetrakis(2,3,4,6-tetrafluorophenyl)borate,
triethylammonium tetrakis(2,3,4,6-tetrafluorophenyl)borate,
tritopylammonium tetrakis(2,3,4,6-tetrafluorophenyl)borate,
tri(n-butyl)ammonium tetrakis(2,3,4,6-tetrafluorophenyl)borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-diethylanilinium tetrakis(2,3,4,6-tetrafluorophenyl)borate, and
N,N-dimethyl-(2,4,6-trimethylanilinium) tetrakis(2,3,4,6-tetrafluorophenyl)borate.

Dialkyl ammonium salts such as:
di-(i-propyl)ammonium tetrakis(pentafluorophenyl)borate, and
dicyclohexylammonium tetrakis(pentafluorophenyl)borate.

Tri-substituted phosphonium salts such as:
triphenylphosphonium tetrakis(pentafluorophenyl)borate,
tri(o-tolyl)phosphonium tetrakis(pentafluorophenyl)borate, and
tri(2,6-dimethylphenyl)phosphonium tetrakis(pentafluorophenyl)borate.

Preferred are tetrakis(pentafluorophenyl)borate salts of long chain alkyl mono- and disubstituted ammonium complexes, especially $C_{14}$–$C_{20}$ alkyl ammonium complexes, especially methyldi(octadecyl)ammonium tetrakis(pentafluorophenyl)borate and methyldi(tetradecyl)ammonium tetrakis(pentafluorophenyl)borate.

Especially preferred activating cocatalysts are tris(pentafluorophenyl)borane, $(R^1{}_2NHCH_3)^+(C_6H_4OH)B(C_6F_5)_3{}^-$, $(R^1{}_2NHCH_3)^+B(C_6F_5)_4{}^-$, or $[(C_6H_5)NHR^2{}_2]^+B(C_6F_5)_4{}^-$, where $R^1$ independently each occurrence is a substituted or unsubstituted saturated hydrocarbyl group having from 12 to 30 carbon atoms, and $R^2$ independently each occurrence is a substituted or unsubstituted saturated hydrocarbyl group having from 1 to 8 carbon atoms.

Another suitable ion forming, activating cocatalyst comprises certain imidazolide, substituted imidazolide, imidazolinide, substituted imidazolinide, benzimidazolide, or substituted benzimidazolide anions depicted schematically as follows:

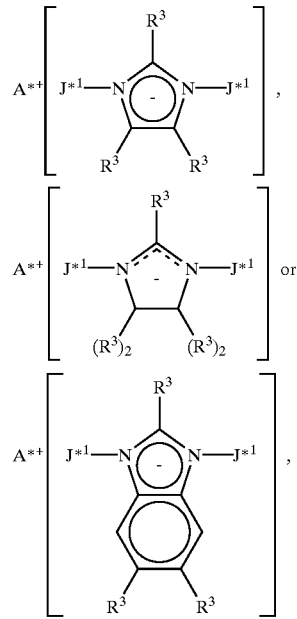

wherein:

$A^{*+}$ is a monovalent cation, preferably a trihydrocarbyl ammonium cation, containing one or two $C_{10-40}$ alkyl groups, especially the methylbis(tetradecyl)ammonium- or methylbis(octadecyl)ammonium-cation, $R^3$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^{*1}$ is tris(pentafluorophenyl)borane or tris(pentafluorophenyl)alumane).

Another suitable ion forming, activating cocatalyst comprises a salt of a cationic oxidizing agent and a noncoordinating, compatible anion represented by the formula:

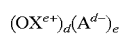

wherein:

$OX^{e+}$ is a cationic oxidizing agent having a charge of e+;

e is an integer from 1 to 3; and $A^{d-}$ and d are as previously defined.

Examples of cationic oxidizing agents include: ferrocenium, hydrocarbyl-substituted terrocenium, $Ag^+$ and $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$^+A^-$ wherein:

$^+$ is a $C_{1-20}$ carbenium ion; and $A^-$ is as previously defined. A preferred carbenium ion is the trityl cation, that is, triphenylmethylium.

A further suitable ion forming, activating cocatalyst comprises a compound which is a salt of a silylium ion and a noncoordinating, compatible anion represented by the formula:

$R_3Si^+A^-$ wherein:

R is $C_{1-10}$ hydrocarbyl, and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem. Comm.*, 1993, 383–384, as well as Lambert, J. B., et al., *Organometallics*, 1994, 13, 2430–2443. The use of the above silylium salts as activating cocatalysts for addition polymerization catalysts is disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected. Suitable supporting electrolytes are salts comprising a cation and a compatible, noncoordinating anion, $A^-$.

Preferred supporting electrolytes are salts corresponding to the formula $G^+A^-$;

wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra(n-butylammonium)- and tetraethylammonium-cations.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl)borates having from 1 to 10 carbons in each hydrocarbyl or perfluoroaryl group, especially tetra(n-butylammonium)tetrakis-(pentafluorophenyl)borate.

A further recently discovered electrochemical technique for generation of activating cocatalysts is the electrolysis of a disilane compound in the presence of a source of a noncoordinating compatible anion. This technique is more fully disclosed in U.S. Pat. No. 5,372,682.

The foregoing electrochemical activating technique and activating cocatalysts may also be used in combination. An especially preferred combination is a mixture of a tri(hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)borane, where used as an activating cocatalyst, is employed in a molar ratio to the metal complex of form 0.5:1 to 10:1, more preferably from 1:1 to 6:1, most preferably from 1:1 to 5:1. The remaining activating cocatalysts are generally employed in approximately equimolar quantity with the metal complex.

Suitable polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1,1-hexene, 1-octene, and combinations of ethylene and/or propene with one or more of such other alpha-oletins. Other preferred monomers include styrene, halo- or alkyl substituted styrenes, tetrafluoroethylene, vinylcyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for solution phase, slurry, gas phase and high pressure Ziegler-Natta or Kaminsky-Sinn type polymerization reactions. Examples of such well known polymerization processes are depicted in U.S. Pat. No. 5,084,534, U.S. Pat. No. 5,405,922, U.S. Pat. No. 4,588,790, U.S. Pat. No. 5,032,652, U.S. Pat. No. 4,543,399, U.S. Pat. No. 4,564,647, U.S. Pat. No. 4,522,987, and elsewhere. Preferred polymerization temperatures are from 0–250° C. Preferred polymerization pressures are from atmospheric to 3000 atmospheres. Molecular weight control agents can be used in combination with the present cocatalysts. Examples of such molecular weight control agents include hydrogen, silanes or other known chain transfer agents. The catalyst composition may be used by itself (homogeneously) or supported on an inert support such as silica, alumina or a polymer.

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. Where stated, the term "room temperature" refers to a temperature from 20 to 25° C., the term "overnight" refers to a time from 12 to 18 hours, and the term "mixed alkanes" refers to a mixture of propylene oligomers sold by Exxon Chemicals Inc. under the trade designation Isopar™ E.

$^1$H and $^{13}$C NMR spectra were recorded on a Varian XL (300 MHz) spectrometer. Chemical shifts were determined relative to TMS or through the residual $CHCl_3$ in $CDCl_3$ or the residual $C_6HD_5$ in $C_6D_6$, relative to TMS. Solvents were used following passage through double columns charged with activated alumina and alumina supported mixed metal oxide catalyst (Q-50® catalyst, available from Engelhard Corp.). The compounds n-BuLi, Grignard reagents were all used as purchased from commercial sources in an appropriate solvent and used as received. All syntheses were performed under dry nitrogen atmosphere using a combination of glove box and high vacuum techniques. The drawings of lithium complexes are simplified and are not intended to accurately represent the compound's hapticity.

EXAMPLE 1

Preparation of Dichloro(N-(1,1-dimethylethyl)-1-((1,2,3,3a,7a-η)-5-methoxy-3-(1-pyrrolidino)-1H-inden-1-yl)-1,1-dimethylsilanaminato(2-)-N)titanium Step 1 Preparation of 1-(5-Methoxy-1H-inden-3-yl) pyrrolidine.

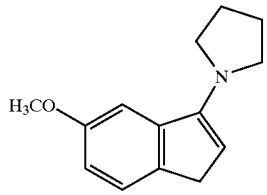

6-Methoxy-1-indenone (7.30 g, 45.01 mmol) was dissolved in 20 mL of toluene in a flask equipped with a Dean-Stark adapter. To this solution, 18.8 mL (225 mmol) of pyrrolidine was added followed by 0.5 g of $P_2O_5$. The reaction mixture was refluxed for approximately 5 hours. At this time the finger of the Dean-Stark adapter (10 mL capacity) was emptied and 10 additional mL of pyrrolidine were added to the flask. After 14 hrs under reflux, GC analysis showed complete conversion to 1-(5-methoxy-1H-inden-3-yl)pyrrolidine. The flask was cooled to room temperature and the solvent was evaporated in vacuum leaving a brown-red oil. This oil was dissolved in 10 mL of ether followed by 60 mL of hexane. This solution was cooled to −27° C. overnight. The resulting solid was filtered off and the solvent was evaporated from the solution leaving 8.15 g of the desired product as a red oil. Yield was 84 percent.

$^1$H NMR ($C_6D_6$) δ 1.54 (m, 4H), 3.20 (m, 4H), 3.27 (s, 2H), 3.47 (s, 3H), 5.09 (s, 1H), 6.75 (dd, 1H, $^3J_{H-H}$=8.0 Hz, $^3J_{H-H}$=2.2 Hz), 7.22 (d, 1H, $^3J_{H-H}$=8.0 Hz), 7.38 (d, 1H, $^3J_{H-H}$=2.2 Hz). $^{13}$C{$^1$H} NMR ($C_6D_6$) δ 25.32, 35.04, 50.19, 55.07, 102.08, 107.77, 109.95, 124.55, 137.70, 143.98, 150.47, 159.13. GC-MS: Calcd for $C_{14}H_{17}NO$: 215.13, found 215.15.

Step 2 Preparation of (5-Methoxy-3-(1-pyrrolidino)-1H-inden-1-yl)lithium

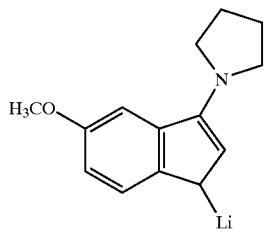

1-(5-methoxy-1H-inden-3-yl)pyrrolidine (8.15 g, 37.9 mmol) was dissolved in 80 mL of hexane and 23.7 mL of 1.6 M n-BuLi were added dropwise via syringe over a 5 min period giving an orange precipitate. The reaction mixture was stirred for 2 h, filtered, washed with 60 mL of hexane and allowed to dry in vacuum to afford the desired product as a orange solid (7.26 g, 87 percent yield).

Step 3 Preparation of N-(1,1-Dimethylethyl)-1-(5-methoxy-3-(1-pyrrolidino)-1H-inden-1-yl)-1,1-dimethylsilanamine

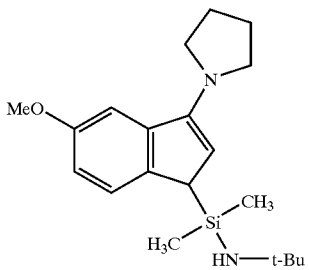

(5-Methoxy-3-(1-pyrroldino)-1H-inden-1-yl)lithium (4.00 g, 18.08 mmol) was dissolved in 40 mL of THF and added dropwise to a solution of N-(tert-butyl)-N-(1-chloro-1,1-dimethylsilyl)amine (4.2 g, 25.3 mmol) in 120 mL of THF over a 25 min period, with stirring continued for 24 h. The solution was evaporated in vacuum to give a dark red oil which was dissolved in hexane (40 mL). LiCl was filtered from this solution and the solvent was removed in under vacuum to give 6.20 g of product as a dark red oil. (99 percent yield).

$^1$H NMR ($C_6D_6$) δ −0.03 (s, 3H), 0.08 (s, 3H), 0.57 (s, 1H), 1.12 (s, 9H), 1.66 (m, 4H), 3.24 (m, 4H), 3.34 (d, 1H, $^3J_{H-H}$=1.8 Hz), 3.51 (s, 3H), 5.41 (d, 1H, $^3J_{H-H}$=1.8 Hz), 6.84 (dd, 1H, $^3J_{H-H}$=8.3 Hz, $^3J_{H-H}$=2.2 Hz), 7.35 (d, 1H, $^3J_{H-H}$=2.2 Hz), 7.46 (d, 1H, $^3J_{H-H}$=8.3 Hz), $^{13}C\{^1H\}$ NMR ($C_6D_6$) δ −0.76, 0.33, 25.22, 34.03, 42.57, 49.50, 50.72, 55.05, 106.62, 106.68, 110.33, 124.05, 139.19, 142.75, 149.36, 158.13.

Step 4 Preparation of (1-(((1,1-Dimethylethyl)amino)dimethylsilyl)-5-methoxy-3-(1-pyrrolidino)-1H-inden-1-yl)lithium, Lithium Salt

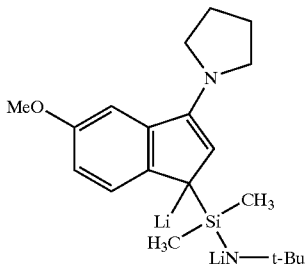

6.2 g (18.0 mmol) N-(1,1-dimethylethyl)-1-(5-methoxy-3-(1-pyrrolidino)-1H-inden-1-yl)-1,1-dimethylsilanamine were combined with 80 mL of hexane. To this solution 24.7 mL (39.6 mmol) of n-BuLi (1.6 M) were added dropwise. Upon complete addition of the n-BuLi, the solution was stirred for 5 h at room temperature. The resulting precipitate was collected via filtration, washed with 60 mL of hexane to give 6.45 g of the desired product as a yellow solid. Yield was 98 percent.

Step 5 Preparation of Dichloro(N-(1,1-dimethylethyl-1-((1,2,3,3a,7a-η)-5-methoxy-3-(1-pyrrolidino)-1H-inden-1-yl)-1,1-dimethylsilanaminato(2-)-N)titanium

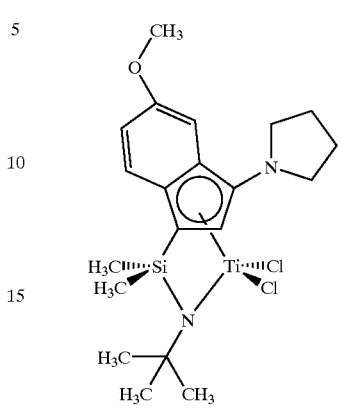

4.68 g (12.6 mmol) Of $TiCl_3(THF)_3$ were suspended in 80 mL of THF. To this solution, 4.5 g (12.6 mmol) of (1-(((1,1-imethylethyl)amino)dimethylsilyl)-5-methoxy-3-(1-pyrrolidino)-1H-inden-1-yl)lithium dissolved in 40 mL of THF were added within 5 min. The solution was then stirred for 50 min. After this time, 2.28 g of $PbCl_2$ (8.21 mmol) were added and the solution was stirred for 12 h. The THF was then removed under reduced pressure. The residue was then extracted with 120 mL of toluene, the solution was filtered, and the toluene was removed under reduced pressure. The residue was then titrated with 60 mL of hexane and the precipitate was collected via filtration on a frit, washed with 60 mL of hexane and dried under vacuum to yield 3.87 g of dichloro(N-(1,1-dimethylethyl)-1-((1,2,3,3a,7a-η)-5-methoxy-3-(1-pyrrolidino)-1H-inden-1-yl)-1,1-dimethylsilanaminato(2-)-N)titanium as a black microcrystalline solid. Yield was 66 percent.

$^1$H NMR ($C_6D_6$) δ 0.54 (s, 3H), 0.61 (s, 3H), 1.39 (s, 9H), 1.54 (m, 4H), 3.32 (s, 2H), 3.40 (s, 3H), 3.68 (m, 2H), 5.68 (s, 1H), 6.97 (s, 1H), 6.99 (d, 1H, $^3J_{H-H}$=9.1 Hz), 7.48 (d, 1H, $^3J_{H-H}$=9.1 Hz). $^{13}C\{^1H\}$ NMR ($C_6D_6$) δ 1.46, 3.58, 25.82, 33.00, 50.52, 55.06, 60.73, 92.75, 103.48, 107.76, 122.61, 129.25, 130.21, 130.40, 148.86, 160.35.

EXAMPLE 2

Preparation of (N-(1,1-Dimethylethyl)-1-((1,2,3,3a,7a-η)-5-methoxy-3-(1-pyrrolidinyl)-1H-inden-1-yl)-1,1-dimethylsilanaminato(2-)-N)dimethyltitanium

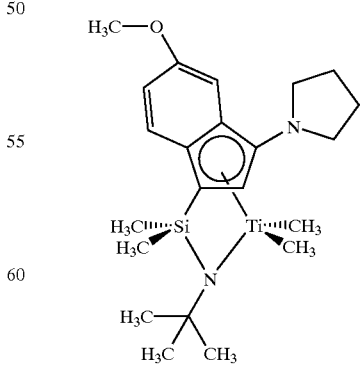

0.70 g (1.5 mmol) Of dichloro(N-(1,1-dimethylethyl)-1-((1,2,3,3a,7a-η)-5-methoxy-3-(1-pyrrolidinyl)-1H-inden-1- yl)-1,1-dimethylsilanaminato(2-)-N)titanium were partly dissolved in 50 mL of Et$_2$O. To this solution, 1.06 mL (3.2 mmol) of MeMgI (3.0 M) were added dropwise while stirring over a 5-minute period. The solution changed color from black to dark red. After the addition of MeMgI was completed, the solution was stirred for 60 minutes. Et$_2$O was removed under reduced pressure and the residue was extracted with hexane (2×20 mL), the solution was filtered and the filtrate was evaporated to dryness under reduced pressure to give 0.450 g of the dimethyl titanium complex (71 percent yield) as a red solid.

$^1$H NMR (C$_6$D$_6$) δ 0.15 (s, 3H), 0.50 (s, 3H), 0.63 (s, 3H), 0.79 (s, 3H), 1.53 (s, 9H), 1.58 (m, 4H), 3.43 (m, 2H), 3.43 (s, 3H), 3.51 (m, 3H), 5.49 (s, 1H), 6.88 (dd, 1H, $^3J_{H-H}$=9.1 Hz, $^4J_{H-H}$=1.9 Hz), 7.11 (d, 1H, $^3J_{H-H}$=1.9 Hz), 7.39 11 (d, 1H, $^3J_{H-H}$=9.1 Hz). $^{13}$C{$^1$H} NMR (C$_6$D$_6$) δ 2.29, 4.44, 25.96, 34.70, 48.49, 50.53, 53.78, 54.87, 57.77, 83.72, 102.52, 105.64, 119.36, 125.97, 129.52, 143.60, 158.37.

EXAMPLE 3

Preparation of Cyclopentadienyl(N-(1,1-dimethylethyl)-1,1-dimethyl-1-((1,2,3,3a,7a-η)-5-methoxy-3-(1-pyrrolidino)-1H-inden-1-yl)silanaminato(2-)-N)titanium

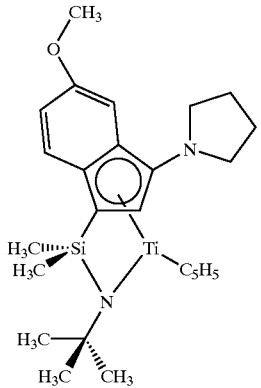

To a well-stirred solution of 2.822 g of bis (cyclopentadienyl)titanium chloride (13.22 mmol) in about 120 mL of THF were slowly added 4.900 g of the dilithium salt of (N-(1,1-dimethylethyl)-1,1-dimethyl-1-(5-methoxy-3-pyrrolidino-1H-inden-1-yl)silanamine (96 percent pure, 13.22 mmol) as a powder over the course of about 30 minutes. The reaction mixture changed from green to yellow-brown and was stirred overnight. The solvents were removed under reduced pressure and the residue was extracted with hexane and the resulting solution was filtered to give a yellow-brown-greenish solution. The product was fractionated and the first fraction was reextracted with hexane and refiltered. The solvent was removed to give a dark solid. This product was slurried in hexane, chilled in a freezer overnight, then filtered and the solids were washed with cold hexane, then dried under reduced pressure to yield 1.223 g of the desired product as a dark olive green powder.

ESR showed a signal at g=1.978 consistent with a Ti(III) complex. Magnetic susceptibility (Evans' method): 1.62 $\mu_B$.

EXAMPLE 4

Preparation of Chloro(cyclopentadienyl)(N-(1,1-dimethylethyl)-1,1-dimethyl-1-((1,2,3,3a,7a-η)-5-methoxy-3-(1-pyrrolidino)-1H-inden-1-yl)silanaminato(2-)-N)titanium

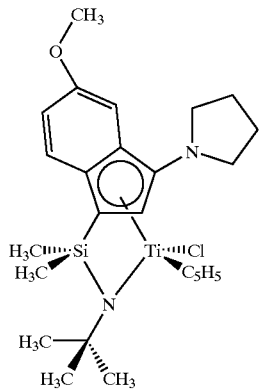

0.2052 g of cyclopentadienyl(N-(1,1-dimethylethyl)-1,1-dimethyl-1-((1,2,3,3a,7a-η)-5-methoxy-3-(1-pyrrolidinyl)-1H-inden-1-yl)silanaminato(2-)-N)titanium (0.450 mmol) were mixed with about 6 mL of CH$_2$Cl$_2$. The color changed instantly to an intense purple. The reaction mixture was stirred for several hours, the solvent was removed under vacuum, the residue was extracted with hexane, filtered and the solvent was removed under reduced pressure to give 0.0688 g of the desired complex as an extremely intensely colored purple powder (31.1 percent yield).

$^1$H (C$_6$D$_6$) δ 0.51 (s, 3H), 0.65 (s, 3H), 1.18 (br, 4H), 1.35 (s, 9H), 3.20 (br, 2H), 3.46 (s, 3H), 3.55 (br, 2H), 5.78, (s, 5H), 5.87, (s, 1H), 6.89 (d, 1H, $^3J_{H-H}$=8.5 Hz), 6.93 (s, 1H), 7.25 (d, 1H, $^3J_{H-H}$=8.6 Hz). $^{13}$C (C$_6$D$_6$) δ 167.5, 155.4, 152.7, 126.9, 121.6, 116.6, 115.2, 107.9, 94.6, 89.1, 60.9, 55.3, 50.7, 33.0, 25.2, 3.9, 2.9. MS: Calcd for C$_{24}$H$_{33}$ClN$_2$SiTi: 490.2 Found: 490.1.

EXAMPLE 5

Preparation of (1-((1,2,3,3a,7a-η)-5-Methoxy-3-(pyrrolidinyl)-1H-inden-1-yl)-N-(1,1-dimethylethyl)-1,1-dimethylsilanaminato(2-)-N)((2-(dimethylamino-N)phenyl)methyl-C)titanium

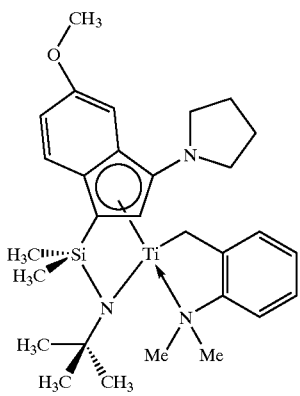

To a solution of 0.5567 g of cyclopentadienyl(N-(1,1-dimethylethyl)-1,1-dimethyl-1-((1,2,3,3a,7a-η)-5-methoxy- 3-(1-pyrrolidinyl)-1H-inden-1-yl)silanaminato(2)-N)
titanium (1.222 mmol) in about 40 mL of Et₂O was slowly
added 0.1811 g of (2-(N,N-dimethylamino)benzyl)lithium
(1.283 mmol) slurried in about 15 mL of Et₂O. The dark
reddish-olive green/brown reaction mixture was stirred
overnight. An additional 0.0156 g of (2-(N,N-dimethylamino)benzyl)lithium (total 1.394 mmol) was
added. After stirring overnight once more and removing the
solvent under reduced pressure, the residue was extracted
with hexane, filtered and concentrated to dryness. About 5
mL of hexane were added to dissolve the product and the
solution was placed in the freezer. The supernatant was
removed and the black solid remaining was dried under
reduced pressure. The yield of product as a black solid was
0.3418 g, 53.3 percent.

MS: Calcd. for $C_{29}H_{42}N_3OSiTi$: 524.3. Found: 523.3.

ESR analysis was consistent with a Ti(III) complex.
Magnetic susceptibility (Evans' method): 1.57 $\mu_B$.

EXAMPLE 6

Preparation of Chloro(1-((1,2,3,3a,7a-η)-5-methoxy-3-pyrrolidinyl-1H-inden-1-yl)-N-(1,1-dimethylethyl)-1,1-dimethylsilanaminato(2-)-N)((2-(dimethylamino)phenyl)methyl)titanium

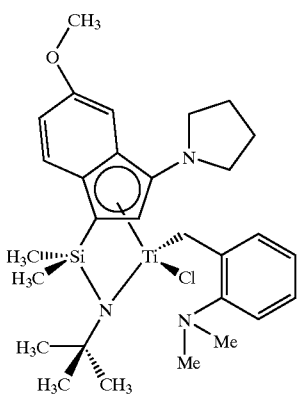

To a solution of 0.079 g of (1-((1,2,3,3a,7a-η)-5-methoxy-3-pyrrolidinyl-1H-inden-1-yl)-N-(1,1-dimethylethyl)-1,1-dimethylsilanaminato(2-)-N)((2-(dimethylamino-N)phenyl)methyl-C)titanium in about 10
mL of Et₂O was added 0.732 g of PbCl₂. The reaction
mixture was stirred for several days. The solvent was
removed and the residue was extracted with hexane, then
filtered and the product was isolated by removal of the
solvents under reduced pressure. NMR spectra showed the
presence of two isomers along with a very small amount of
the (chloro)(cyclopentadienyl) complex.

¹H (C₆D₆) δ 0.67, 0.70, 0.73, 0.84, 1.28, 1.35, 1.40, 1.61,
1.62, 2.1, 2.15, 2.20, 2.29, 2.44, 2.47, 2.58, 2.60, 2.83, 3.22,
3.46, 3.63, 5.15, 5.64, 5.78, 6.35, 6.6–6.78, 6.83–7.0, 7.32,
7.37, 7.78, 7.82. ¹³C (C₆D₆) δ 158.5, 156.3, 154.1, 153.1,
151.1, 149.5, 147.2, 143.3, 131.6, 130.4, 129.4, 127.7,
126.6, 126.4, 125.9, 123.6, 123.4, 122.7, 121.6, 120.1,
118.4, 118.1, 117.5, 116.6, 115.2, 107.9, 102.7, 101.7, 101.4,
100.3, 98.7, 97.1, 89.2, 72.1, 69.5, 55.3, 54.1, 50.8, 50.1,
47.5, 45.3, 35.1, 33.2, 32.1, 30.3, 25.8, 25.4, 24.4, 23.2, 21.0,
14.5, 4.5, 3.2, 2.6, 1.4.

EXAMPLE 7

Preparation of Dichloro(1-((1,2,3,3a,7a-η)-5,6-dimethoxy-3-(1-pyrrolidinyl)-1H-inden-1-yl)-N-(1,1-dimethylethyl)-1,1-dimethylsilanaminato(2-)-N) titanium Step 1 Preparation of 1-(5,6-Dimethoxy-1H-inden-3-yl) pyrrolidine

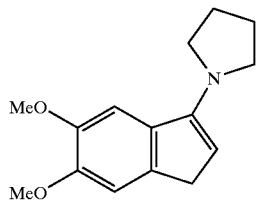

5,6-Dimethoxy-1-indenone (5.1 g, 26.53 mmol) was dissolved in 120 mL of toluene. To this solution 17.7 mL (212
mmol) of pyrrolidine was added followed by 0.5 g of P₂O₅.
The reaction mixture was refluxed for about 20 hours in a
flask equipped with a Dean-Stark adapter. The flask was
cooled to room temperature and the solvent was evaporated
in vacuum leaving a brown-red solid. This solid was
extracted with 50 mL of ether and filtered. The ether was
evaporated leaving a brown solid. This solid was extracted
with 120 mL of hot hexane and filtered. The hexane was
removed and solid was dissolved in a mixture of 30 mL of
toluene and 60 mL of hexane and filtered. The red solution
was cooled to −27° C. overnight. The resulting solid was
recovered by decantation, washed with cold hexane and
dried under reduced pressure to give 2.97 g of 1-(5,6-dimethoxy-1H-inden-3-yl)pyrrolidine. Yield was 46 percent.

¹H NMR (C₆D₆) δ 1.60 (m, 4H), 3.26 (m, 4H), 3.29 (s,
2H), 3.51 (s, 3H), 3.59 (s, 3H), 5.05 (s, 1H), 6.85 (s, 1H),
7.25 (s, 1H). ¹³C{¹H} NMR (C₆D₆) δ 25.39, 35.73, 50.24,
55.67, 56.49, 99.27, 106.85, 109.59, 135.48, 138.70, 148.63,
148.90, 150.61. GC-MS: Calcd for $C_{15}H_{19}NO_2$: 245.14,
found 245.15.

Step 2 Preparation of (5,6-Dimethoxy-3-(1-pyrrolidino)-1H-inden-1-yl)lithium

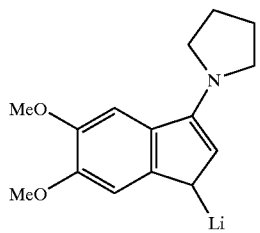

1-(5,6-Dimethoxy-1H-inden-3-yl)pyrrolidine (2.87 g,
11.7 mmol) was dissolved in a mixture of 40 mL of toluene
and 40 mL of hexane then 7.0 mL of 1.6 M n-BuLi was
added dropwise via syringe over a 5 min period. The
reaction mixture was stirred for 3 hrs. After this time, the
solid was filtered, washed with 30 mL of toluene and then
with 60 mL of hexane and dried in vacuum to afford the
desired product as a yellow solid. (2.67 g, 95 percent yield).

Step 3 Preparation of 1-(5,6-Dimethoxy-3-(1-pyrrolidino)-1H-inden-1-yl)-N-(1,1-dimethylethyl)-1,1-dimethylsilanamine

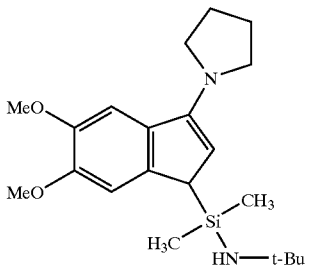

(5,6-Dimethoxy-3-(1-pyrrolidino)-1H-inden-1-yl)lithium (2.67 g, 10.63 mmol) was slurried in 100 mL of THF then added to a solution of N-(tert-butyl)-N-(1-chloro-1,1-dimethylsilyl)amine (2.73 g, 16.47 mmol) in 150 mL of THF over a 25 min period, with stirring continued for 20 h. The solution was evaporated in vacuum to give a dark red oil. The oil was extracted hexane (40 mL), filtered, and the solvent was removed under vacuum to give 3.83 g of 1-(5,6-dimethoxy-3-(1-pyrrolidinyl)-1H-inden-1-yl)-N-(1,1-dimethylethyl)-1,1-dimethylsilanamine as a dark red oil in 96 percent yield.

$^1$H NMR ($C_6D_6$) δ −0.07 (s, 3H), 0.16 (s, 3H), 0.57 (s, 1H), 1.13 (s, 9H), 1.66 (m, 4H), 3.28 (m, 4H), 3.38 (d, 1H, $^3J_{H-H}$=1.7 Hz), 3.60 (s, 3H), 3.65 (s, 3H), 5.34 (d, 1H, $^3J_{H-H}$=1.7 Hz), 7.20 (s, 1H), 7.29 (s, 1H). $^{13}C\{^1H\}$ NMR ($C_6D_6$) δ −1.49, 0.61, 25.24, 34.00, 43.13, 49.48, 50.73, 56.06, 56.31, 103.58, 106.14, 108.93, 134.57, 139.92, 148.11, 148.28, 149.48.

Step 4 Preparation of (1-(((1,1-Dimethylethyl)amino)dimethylsilyl)-5,6-dimethoxy-3-(1-pyrrolidino)-1H-inden-1-yl)dilithium Salt

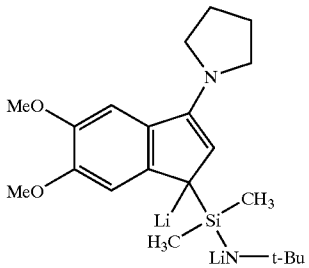

3.68 g (9.82 mmol) of 1-(5,6-dimethoxy-3-(1-pyrrolidino)-1H-inden-1-yl)-N-(1,1-dimethylethyl)-1,1-dimethylsilanamine were combined with a mixture of 60 mL of hexane and 30 mL of toluene. To this solution 12.3 mL (19.6 mmol) of n-BuLi (1.6 M) were added dropwise. The solution was stirred for 7 h at room temperature. The resulting precipitate was collected via filtration, washed with 60 mL of hexane and then dried under reduced pressure to give 3.71 g of the dilithium salt as a yellow solid. Yield was 98 percent.

Step 5 Preparation of Dichloro(1-((1,2,3,3a,7a-η)-5,6-dimethoxy-3-(1-pyrrolidino)-1H-inden-1-yl)-N-(1,1-dimethylethyl)-1,1-dimethylsilanaminato(2-)-N)titanium

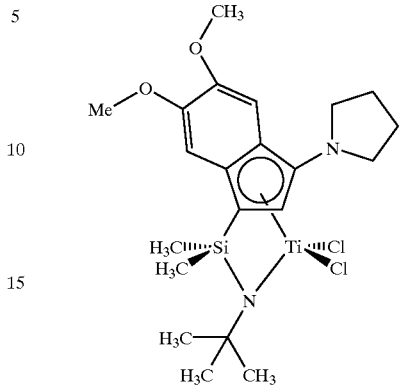

3.557 g (9.6 mmol) Of TiCl$_3$.(THF)$_3$ were suspended in 70 mL of THF. To this solution, 3.71 g (9.6 mmol) of (1-(((1,1-dimethylethyl)amino)dimethylsilyl)-5,6-dimethoxy-3-(1-pyrrolidino)-1H-inden-1-yl)dilithium salt slurried in 40 mL of THF were added within 5 min. The solution was stirred for 50 minutes, then 1.735 g of PbCl$_2$ (6.24 mmol) were added and the solution was stirred for 50 min. THF was then removed under reduced pressure. The residue was then extracted with 120 mL of toluene, the resulting solution was filtered, and the toluene was removed under reduced pressure. The residue was then triturated with 60 mL of hexane and the precipitate was collected via filtration on a frit, washed with 60 mL of hexane and dried under vacuum to yield 3.25 g of the crude product as a dark-green solid. Yield was 69 percent. The complex was recrystallized from a toluene/hexane mixture at −27° C. to give highly pure dichloro(1-((1,2,3,3a,7a-η)-5,6-dimethoxy-3-(1-pyrrolidino)-1H-inden-1-yl)-N-(1,1-dimethylethyl)-1,1-dimethylsilanaminato(2-)-N)titanium.

$^1$H NMR (CD$_2$Cl$_2$) δ 0.65 (s, 3H), 0.82 (s, 3H), 1.29 (s, 9H), 2.04 (m, 4H), 3.68 (m, 2H), 3.81 (s, 3H), 3.91 (s, 3H), 3.98 (m, 2H), 5.54 (s, 1H), 6.77 (s, 1H), 7.10 (s, 1H) $^{13}C\{^1H\}$ NMR (CD$_2$Cl$_2$) δ 1.50, 3.74, 26.10, 32.88, 50.83, 56.00, 56.26, 60.73, 92.56, 103.79, 106.83, 106.02, 122.29, 132.17, 149.43, 152.70, 153.26.

EXAMPLE 8
Preparation of (1-((1,2,3,3a,7a-η)-5,6-Dimethoxy-3-(1-pyrrolidino)-1H-inden-1-yl)-N-(1,1-dimethylethyl)-1,1-dimethylsilanaminato(2-)-N) dimethyltitanium

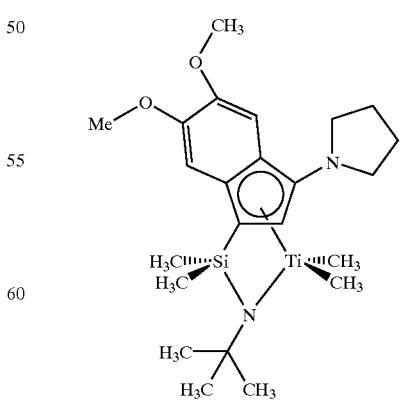

0.3 g (0.61 mmol) of dichloro(1-((1,2,3,3a,7a-η)-5,6-dimethoxy-3-(1-pyrrolidinyl)-1H-inden-1-yl)-N-(1,1- dimethylethyl)-1,1-dimethylsilanaminato(2-)-N)titanium were partly dissolved in 50 mL of Et$_2$O. While stirring the solution, 0.85 mL (1.28 mmol) of MeLi (1.5 M) were added dropwise over a 5 minute period. The solution changed color from black to dark red. The solution was stirred for an additional 2 hrs. The solvent was removed under reduced pressure and the residue was extracted with hexane (3×40 mL), then filtered. The filtrate was evaporated to dryness under reduced pressure to give 0.147 g (53 percent yield) of the desired product as a dark red crystalline solid.

$^1$H NMR (C$_6$D$_6$): δ 0.19 (s, 3H), 0.54 (s, 3H), 0.69 (s, 3H), 0.77 (s, 3H), 1.56 (s, 9H), 1.59 (m, 4H), 3.34 (m, 2H), 3.36 (s, 3H), 3.50 (s, 3H), 3.51 (m, 2H), 5.42 (s, 1H), 6.76 (s, 1H), 7.09 (s, 1H). $^{13}$C{$^1$H} (C$_6$D$_6$): δ 2.41, 4.76, 25.99, 34.76, 47.83, 50.49 52.51, 55.07, 55.62, 57.51, 82.52, 103, 44, 103.81, 106.12, 119, 63, 129.79, 143.61, 151.45, 151.65.

EXAMPLE 9

Preparation of Dichloro(N-(1,1-dimethylethyl)-1,1-dimethyl-5-((4a,5,6,7,7a-η)-6-methyl-5H-indeno(5,6-d)-1,3-dioxol-5-yl)silanaminato(2-)-N)titanium Step 1 Preparation of 1,3-Dioxol-5-(N,N-dimethylamino)-6-methyl-2,5H-s-indacene

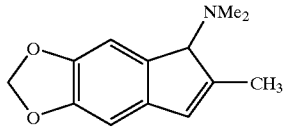

Phosphorus oxychloride (23.2 mL, 0.249 moles) was added dropwise by syringe while stirring to dimethylformamide (98 mL, 1.264 moles) in an ice bath under argon for about 20 minutes. Isosafrole (30.0 mL, 0.207 moles) was added dropwise by addition funnel to this stirring solution. After addition was completed, the reaction mixture was heated to 110° C. for three hours. The reaction mixture was then poured into 800 mL of ice, washed with three 300 mL portions of diethyl ether, and the aqueous layer was made basic (pH=8) by the addition of 10 percent aqueous NaOH (about 40 g NaOH in 400 mL of water). The desired product was then extracted with four 300 mL portions of ether and the combined organic extracts were dried over MgSO$_4$. The ether was removed under reduced pressure leaving a medium brown solid. The product was recrystallized from hexane to give 17.0 g of a light yellow solid. Yield was 51.8 percent.

$^1$H NMR (C$_6$D$_6$): δ 1.91 (s, 3H); 2.18 (s, 6H); 3.79 (s, 1H); 5.42 (s, 1H); 5.44 (s, 1H); 6.04 (s, 1H); 6.65 (s, 1H); 7.04 (s, 1H). $^{13}$C{$^1$H} NMR (C$_6$D$_6$): δ 40.92, 74.08, 100.83, 101.96, 106.73, 127.25, 137.39, 138.62, 145.39, 147.09, 147.55.

Step 2 Preparation of 1,3-Dioxol-6-methyl-2,5,6,7H-s-indacene-5-one

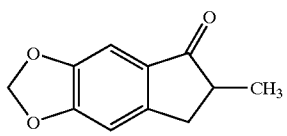

In a 2L flask, 400 mL of ethanol and 400 mL of water were combined and stirred with 36 g of NaOH (0.900 moles). To this mixture, 17.00 g (0.078 moles) of 1,3-dioxol-5-(N,N-dimethylamino)-6-methyl-2,5H-s-indacene were added and the mixture was stirred overnight. The solution became brown/orange in color. Next, 800 mL of water were added to the reaction mixture, and the product was extracted with diethyl ether. The ether layer was washed with 400 mL of a saturated NaCl solution and dried over MgSO$_4$. After removal of the ether, the dark brown/orange oil was distilled to yield a light yellow solid weighing 12.0 g, 80.6 percent.

$^1$H NMR (C$_6$D$_6$): δ 1.09 (d, 3H, $^3$J$_{H\text{-}H}$=7.44 Hz), 2.05–2.11 (dd, 1H, $^3$J$_{H\text{-}H}$=3.42 Hz, $^2$J$_{H\text{-}H}$=16.8 Hz), 2.33 (m, 1H), 2.66–2.71 (dd, 1H, $^3$J$_{H\text{-}H}$=7.68, $^3$J$_{H\text{-}H}$=16.8 Hz), 5.39 (s, 2H), 6.38 (s, 1H), 7.12 (s, 1H). $^{13}$C{$^1$H} NMR (C$_6$D$_6$): δ 16.46, 34.74, 42.39, 102.13, 102.44, 105.68, 131.37, 148.49, 150.35, 154.13, 205.60 GC-MS: Calcd. for C$_{11}$H$_{10}$O$_3$: 190.06, found 190.05.

Step 3 Preparation of 1,3-Dioxol-5-hydroxyl-6-methyl-2,5,6,7H-s-indacene

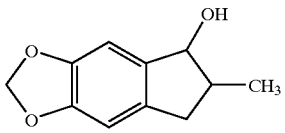

In a 250 mL round bottom flask, 2.438 g (64.45 mmol) of sodium borohydride were stirred in about 150 mL of anhydrous ethanol. To this stirring solution, 12.01 g (63.19 mmol) of 1,3-dioxol-6-methyl-2,5,6,7H-s-indacene-5-one was added and the solution was stirred overnight at room temperature. Water was added (200 mL) to the reaction mixture and stirred about 10 minutes. The solution was then extracted with ethyl acetate (3×200 mL). The ethyl acetate layer was further washed twice with about 200 mL each portion and then dried with MgSO$_4$. Ethyl acetate was then removed under reduced pressure resulting in the isolation of 10.65 g of the desired product as a white solid. Yield was 87.7 percent.

GC-MS: Calcd for C$_{11}$H$_{12}$O$_3$: 192.08, found 192.05.

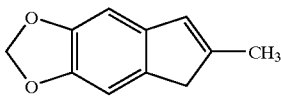

In a 250 mL round bottom flask 6.00 g (31.2 mmol) of 1,3-dioxol-5-hydroxyl-6-methyl-2,5,6,7H-s-indacene was dissolved in 100 mL of anhydrous dimethylsulfoxide (DMSO) and the mixture was refluxed for about 5 hours. The solution was poured into 250 mL of ice, then extracted with diethyl ether (3×200 mL). The combined organic fractions were dried over MgSO$_4$. The ether was removed under reduced pressure leaving a light tan/orange solid. This product was recrystallized from cold hexane yielding 4.15 g of highly pure product.

$^{13}$C{$^1$H} NMR (C$_6$D$_6$): δ 16.48, 42.45, 100.70, 101.45, 105.38, 127.35, 137.05, 140.02, 144.32, 145.42, 147.01.

Step 5 Preparation of (3,5-Dioxol-8-methyl-1,4H-s-indacene-1-yl)lithium

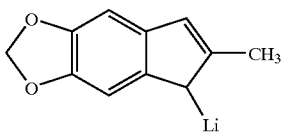

1,3-dioxol-6-methyl-2,5H-s-indacene (4.150 g, 23.8 mmol) was dissolved in 150 mL of hexane and 14.9 mL of 1.6 M n-BuLi were added dropwise via syringe over a 15 min period. The reaction mixture was stirred for 20 h. After this time the solid was filtered, washed with 60 mL of hexane and allowed to dry in vacuum to afford the desired product as an off-white solid (3.64 g) in 85 percent yield.

Step 6 Preparation of (N-(1,1-Dimethylethyl)amino)(3,5-dioxol-8-methyl-1,4H-s-indacene-1-yl)dimethylsilane

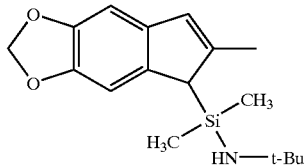

In a 250 mL round bottom flask, 2.76 g (16.65 mmol) of N-(tert-butyl)-N-(1-chloro-1,1-dimethylsilyl)amine were stirred in about 75 mL of THF. The solution was stirred while 2.00 g (11.10 mmol) of 3,5-dioxol-8-methyl-1,4H-s-indacene-1-yl)lithium in about 20 mL THF were added dropwise. The reaction mixture was stirred overnight. The volatile components were removed under reduced pressure and the residue was extracted with hexane. After filtration, the volatile components were removed under vacuum leaving a light brown/green oil weighing 3.14 g, 92.9 percent yield.

$^{13}C\{^1H\}$ NMR ($C_6D_6$): δ 0.29, 0.82, 1.11, 1.20, 18.19, 33.85, 49.54, 51.12, 100.60, 100.72, 100.95, 105.08, 125.90, 139.06, 139.41, 144.75, 146.22.

Step 7 Preparation of (5-(((1,1-Dimethylethyl)amino) dimethylsilyl)-5H-6-methyl-indeno(5,6-d)-1,3-dioxol-5-yl) lithium, Lithium Salt

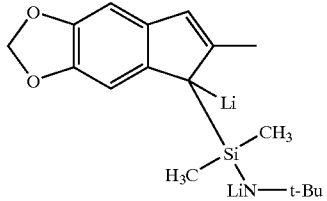

In a 100 mL round bottom flask, 3.14 g (10.3 mmol) of (N-(1,1-dimethylethyl)amino)(3,5-dioxol-8-methyl-1,4H-s-indacene-1-yl)dimethylsilane were stirred in about 75 mL of hexane. To this stirring solution 8.26 mL (20.6 mmol) of 2.5 M n-BuLi were added dropwise by syringe. After stirring for 3 days, the resulting precipitate was filtered, washed with hexane, and dried under vacuum to give a light tan solid weighing 3.51 g.

Step 8 Preparation of Dichloro(N-(1,1-dimethylethyl)-1,1-dimethyl-((4a,5,6,7,7a-η)-6-methyl-5H-indeno(5,6-d)-1,3-dioxol-5-yl)silanaminato(2-)-N)titanium

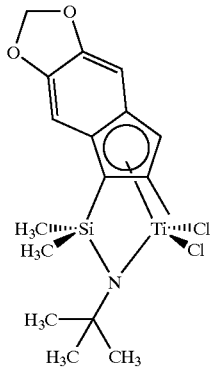

0.924 g (2.92 mmol) of (5-(((1,1-dimethylethyl)amino) dimethylsilyl)-5H-6-methyl-indeno(5,6-d)-1,3-dioxol-5-yl) lithium, lithium salt were added to a slurry of 1.08 g (2.92 mmol) of $TiCl_3.(THF)_3$ In THF. The reaction product was stirred about one 5 hour, then 0.528 g (1.90 mmol) of $PbCl_2$ were added and the mixture was stirred another hour. The volatile components were then removed under reduced pressure and the residue was extracted with toluene. After filtration, the volatile components were removed under reduced pressure. Solids were collected on a frit, and washed with hexane to yield a dark red/brown solid that was dried under vacuum. Recrystallization of the product gave 450 mg of highly pure complex.

$^1H$ NMR ($C_6D_6$): δ 0.40 (s, 3H), 0.44 (s, 3H), 1.34 (s, 9H), 2.11 (s, 3H), 5.14 (s, 1H), 5.16 (s, 1H), 6.54 (s, 1H), 6.55 (s, 1H), 7.00 (s, 1H). $^{13}C\{^1H\}$ NMR ($C_6D_6$): δ 4.89, 5.00, 19.52, 32.46, 62.09, 93.39, 101.20, 101.61, 102.94, 121.58, 132.54, 133.88, 143.97, 151.57, 151.87.

EXAMPLE 10

Preparation of (N-(1,1-Dimethylethyl-1,1-dimethyl-5-((4a,5,6,7,7a-η)-6-methyl-5H-indeno(5,6-d)-1,3-dioxol-5-yl)silanaminato(2-)-N)dimethyltitanium

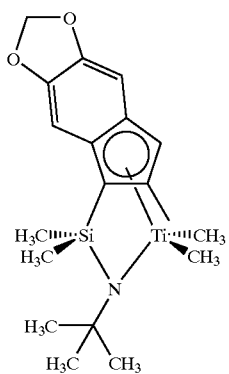

0.30 g (0.72 mmol) of dichloro(N-(1,1-dimethylethyl)-1,1-dimethyl-5-((4a,5,6,7,7a-η)-6-methyl-5H-indeno(5,6-d)-1,3-dioxol-5-yl)silanaminato(2-)-N)titanium were dissolved in 30 mL of $Et_2O$. To this solution, 0.52 mL (1.57 mmol) of MeMgI (3.0 M) were added dropwise over a 5 minute period. The solution changed color from brown-red to green-yellow. After the addition of MeMgI was completed, the solution was stirred for 60 minutes. The $Et_2O$ was removed under reduced pressure and the residue was extracted with hexane (2×20 mL), the solution was filtered, and the filtrate was evaporated to dryness under reduced pressure to give 0.168 g of the desired product (62 percent yield) as a yellow solid.

$^{13}$C {$^1$H} (C$_6$D$_6$) δ 5.72, 5.80, 18.52, 34.41, 50.59, 54.92, 57.88, 89.42, 100.81, 100.89, 103.38, 115.83, 130.69, 140.08, 149.33, 149.68.

EXAMPLE 11

Preparation of Dichloro(N-(1,1-dimethylethyl)-1,1-dimethyl-5-((4a,5,6,7,7a-η)-5-(N,N-dimethylamino)-6-methyl-5H-indeno(5,6-d)-1,3-dioxol-5-yl)silanaminato(2-)-N)titanium Step 1 Preparation of (7-(Dimethylamino)-6-methyl-5H-indeno(5,6-d)-1,3-dioxol-5-yl)lithium

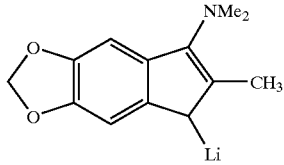

In a 250 mL round bottom flask, 6.347 g (29.91 mmol) of (7-(N,N-dimethylamino)-6-methyl-5H-indeno(5,6-d)-1,3-dioxol-5-yl)lithium were stirred in 20 mL of toluene. After adding 100 mL of hexane to this stirring solution, 12.0 mL of 2.5 M n-BuLi (29.91 mmol) were added slowly by syringe and the reaction mixture was stirred overnight. The solids were filtered off and dried under vacuum to give 5.404 g (80.9 percent yield) of the desired product.

Step 2 Preparation of (N-(1,1-Dimethylethyl)amino)(3,5-dioxol-7-(N,N-dimethylamino)-8-methyl-1,4H-s-indacene-1-yl)dimethylsilane

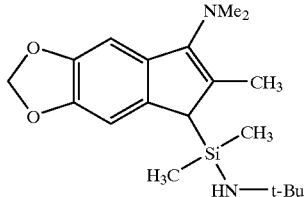

In a 100 mL round bottom flask, 2.02 mL (12.11 mmol) of N-(tert-butyl)-N-(1-chloro-1,1-dimethylsilyl)amine were stirred in about 50 mL of THF. A solution of (7-(dimethylamino)-6-methyl-5H-indeno(5,6-d)-1,3-dioxol-5-yl)lithium (1.802 g, 8.07 mmol) dissolved in about 10 mL of THF was added dropwise. After stirring overnight, the volatile components were removed under reduced pressure. The remaining solids were washed with hexane and filtered. The volatile components were removed from the filtrate leaving the product as an orange/brown oil weighing 2.82 g.

$^1$H NMR (C$_6$D$_6$): δ ⁻0.03 (s, 3H); 0.01 (s, 3H); 1.03 (s, 9H); 2.13 (s, 3H); 2.76 (s, 6H); 2.99 (s, 1H); 5.47 (s, 1H); 5.50 (s, 1H); 7.09 (s, 1H); 7.16 (s, 1H), $^{13}${$^1$H} NMR (C$_6$D$_6$): δ 0.20, 0.27, 0.60, 15.51, 33.65, 33.79, 43.36, 48.27, 49.13, 49. 41, 100.46, 100.58, 105.21, 132.06, 137.37, 137.51, 144.73, 145.94.

Step 3 Preparation of (7-(Dimethylamino)-5-(((1,1-dimethylethyl)amino)dimethylsilyl)-6-methyl-5H-indeno(5,6-d)-1,3-dioxol-5-yl)lithium, Lithium Salt

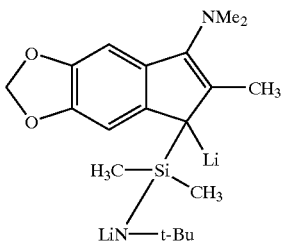

In a 250 mL round bottom flask, 3.035 g (8.76 mmol) 1-(7-(dimethylamino)-6-methyl-5H-indeno(5,6-d)-1,3-dioxol-5-yl)-N-(1,1-dimethylethyl)silanamine was stirred in about 100 mL of hexane. 7.0 mL of 2.5 M n-BuLi (17.52 mmol) were added by syringe and the reaction mixture was stirred overnight. The solids were then filtered off, washed with excess hexane and dried under vacuum to give 3.23 g of product.

Step 4 Preparation of Dichloro(1-((4a,5,6,7,7a-η)-7-(dimethylamino)-6-methyl-5H-indeno(5,6-d)-1,3-dioxol-5-yl)-N-(1,1-dimethylethyl)-1,1-dimethylsilanaminato(2-)-N)titanium.

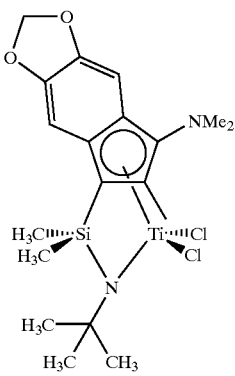

In a drybox 1.031 g (2.78 mmol) of TiCl$_3$(THF)$_3$ were suspended in about 50 mL of THF in a 100 mL round bottom flask. 1.000 g of (2.78 mmol) (7-(dimethylamino)-5-(((1,1-dimethylethyl)amino)dimethylsilyl)-6-methyl-5H-indeno(5,6-d)-1,3-dioxol-5-yl)lithium, lithium salt was added as a solid and the reaction mixture was stirred for 1 ½ h. 0.503 g (1.81 mmol) Of PbCl$_2$ was then added and stirring was continued for another hour. Solvent was then removed under reduced pressure. The residue was extracted with toluene, the solution was filtered and the solvent was removed under reduced pressure. The residue was extracted with hexane and filtered. The volatile components were removed under reduced pressure leaving the desired product as a brown/black solid.

$^{13}$C{$^1$H} NMR (C$_6$D$_6$): δ 83, 56.00, 56.26, 60.73, 92.56, 103.79, 106.83, 107.02, 122.29, 132.17, 149.43, 152.70, 153.26.

EXAMPLE 12

Preparation of (1-((4a,5,6,7,7a-η)-7-(Dimethylamino)-6-methyl-5H-indeno(5,6-d)-1,3-dioxol-5-yl)-N-(1,1-dimethylethyl)-1,1-dimethylsilanaminato(2-)-N)dimethyltitanium

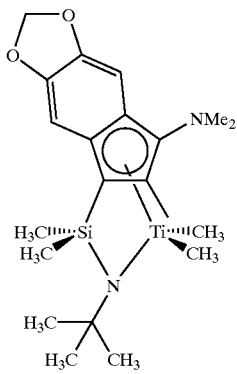

Dichloro(1-((4a,5,6,7,7a-η)-7-(dimethylamino)-6-methyl-5H-indeno(5,6-d)-1,3-dioxol-5-yl)-N-(1,1-dimethylethyl)-1,1-dimethylsilanaminato(2-)-N)titanium (0.5 mmol) was dissolved in 30 mL of Et$_2$O. To this solution, MeMgI (1.0 mmol) was added dropwise over a 5 minute period. After addition of MeMgI was completed, the solution was stirred for 60 minutes. Et$_2$O was removed under reduced pressure and the residue was extracted with hexane (2×20 mL), the solution was filtered, and the filtrate was evaporated to dryness under reduced pressure to give the product as a yellow solid.

EXAMPLE 13

Preparation of Dichloro(1-((1,2,3,3a,7a-η)-5,6-dimethoxy-1H-inden-1-yl-N-(1,1-dimethylethyl)-1,1-dimethylsilanaminato(2-)-N)titanium Step 1 Preparation of (5,6-Dimethoxy-1H-inden-1-yl) lithium.

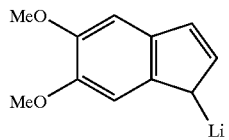

5,6-Dimethoxy-indene (4.82 g, 27.35 mmol) was dissolved in a mixture of 20 mL of toluene and 180 mL of hexane and 16.25 mL of 1.6 M n-BuLi were added dropwise via a syringe over a 5 min period forming a white precipitate. The reaction mixture was stirred for 4 h then filtered. The solids were washed with 60 mL of hexane and allowed to dry under reduced pressure to afford the desired anion as a light pink solid (4.62 g, 98 percent yield).

Step 2 Preparation of 1-(5,6-Dimethoxy-1H-inden-1-yl)-N-(1,1-dimethylethyl)-1,1-dimethylsilanamine

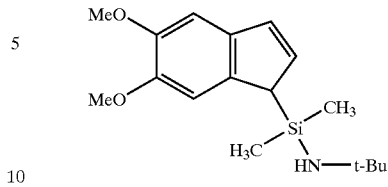

(5,6-Dimethoxy-1H-inden-1-yl)lithium (2.5 g, 13.73 mmol) slurried in 40 mL of THF was added to a solution of N-(tert-butyl)-N-(1-chloro-1,1-dimethylsilyl)amine (3.185 g, 19.22 mmol) in 100 mL of THF over a 25 min period. After stirring for 18 h, the volatile components were removed under reduced pressure. The residue solution was extracted with hexane (40 mL). After filtration the volatile components were removed in under vacuum to give 3.95 g, 94 percent yield of the desired product as a light yellow oil.
$^1$H (C$_6$D$_6$) δ −0.12 (s, 3H), 0.00 (s, 3H), 0.53 (s, 1H), 1.09 (s, 9H), 3.46 (s, 1H), 3.54 (s, 3H), 3.64 (s, 3H), 6.55 (dd, 1H, $^3J_{H-H}$=5.2 Hz, $^3J_{H-H}$=1.7 Hz), 6.85 (d, 1H, $^3J_{H-H}$=4.2 Hz), 6.92 (s, 1H), 7.16 (s, 1H). $^{13}$C{$^1$H} (C$_6$D$_6$) δ −1.36, 0.18, 33.90, 48.66, 49.53, 55.85, 56.27, 105.45, 108.68, 129.20, 134.53, 137.96, 138.22, 148.02, 148.95.

Step 3 Preparation of 1-(((1,1-Dimethylethyl)amino)dimethylsilyl)-5,6-dimethoxy-1H-inden-1-yl)lithium, Lithium Salt.

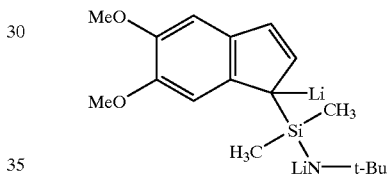

3.80 g (12.44 mmol) Of 1-(5,6-dimethoxy-1H-inden-1-yl)-N-(1,1-dimethylethyl)-1,1-dimethylsilanamine were combined with 100 mL of hexane. To this solution, 15.55 mL (24.88 mmol) of n-BuLi (1.6 M) were added dropwise. The solution was then stirred for 8 h at room temperature. The resulting precipitate was collected via filtration, washed with 60 mL of hexane, then dried under reduced pressure to give 3.95 g of the desired product as a pink colored solid. Yield was 99 percent.

Step 4 Preparation of Dichloro(1-((1,2,3,3a,7a-η)-5,6-dimethoxy-1H-inden-1-yl)-N-(1,1-dimethylethyl)-1,1-dimethylsilanaminato(2-)-N)titanium.

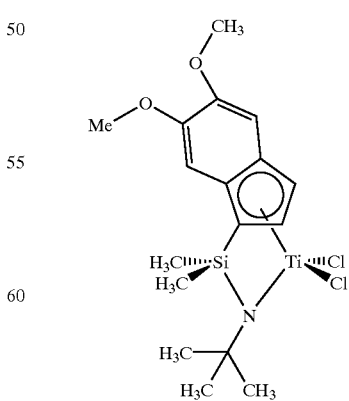

4.58 g (12.4 mmol) Of TiCl$_3$.(THF)$_3$ were suspended in 90 mL of THF. To this slurry 3.92 g (12.4 mmol) of 1-(((1,1-dimethylethyl)amino)dimethylsilyl)-5,6-dimethoxy-1H-inden-1-yl)lithium, lithium salt dissolved in 40 mL of THF was added within 5 min. After stirring for 50 minutes, 2.23 g of PbCl$_2$ (8.0 mmol) were added and the solution was stirred for 50 min. The THF was then removed under reduced pressure. The residue was dissolved in 70 mL of toluene and solution was filtered. Toluene was removed under reduced pressure leaving a sticky brown residue. The residue was triturated with 80 mL of hexane, resulting in the formation of light brown-yellow solid. The solid was collected on a frit, washed with 30 mL of hexane and dried under reduced pressure to give 3.45 g of crude product. The complex was later crystallized from a toluene/hexane mixture at −27° C. to give 1.16 g of the pure product. Yield was 22 percent. The proton NMR shows that the complex and toluene crystallize in a ratio of 1:1.

$^1$H (CD$_2$Cl$_2$) δ 0.41, (s, 3H), 0.62 (s, 3H), 1.37 (s, 9H), 3.30 (s, 3H), 3, 34 (s, 3H), 6.24 (d, 1H, $^3J_{H-H}$=3.2 Hz), 6.51 (s, 1H), 6.77 (s, 1H), 6.93 (d, 1H, $^3J_{H-H}$=3.2 Hz). $^{13}$C{$^1$H} (CD$_2$Cl$_2$) δ 0.91, 3.31, 32.47, 55.26, 55.59, 62.28, 97.30, 103.29, 104.69, 119.01, 127.29, 131.78, 132.75, 154.22, 155.06.

EXAMPLE 14

Preparation of (1-((1,2,3,3a,7a-η)-5,6-Dimethoxy-1H-inden-1-yl)-N-(1,1-dimethylethyl)-1,1-dimethylsilanaminato(2-)-N)dimethyltitanium

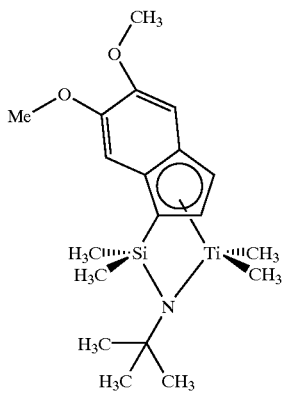

0.19 g (1.42 mmol) of dichloro(1-((1,2,3,3a,7a-η)-5,6-dimethoxy-1H-inden-1-yl)-N-(1,1-dimethylethyl)-1,1-dimethylsilanaminato(2-)-N)titanium were partially dissolved in 50 mL of Et$_2$O. To this solution, 0.63 mL (0.94 mmol) of MeLi (1.5 M) were added dropwise over a 5 minute period. The solution changed color from brown to yellow. The solution was stirred for an additional 60 minutes, then the Et$_2$O was removed under reduced pressure and the residue was extracted with hexane (2×20 mL). The solution was filtered and the filtrate was evaporated to dryness under reduced pressure to give 0.100 g (58 percent yield) of the desired product as a yellow solid.

$^1$H NMR (C$_6$D$_6$): δ −0.02 (s, 3H), 0.43 (s, 3H), 0.59 (s, 3H), 0.85 (s, 3H), 1.51 (s, 9H), 3.32 (s, 3H), 3.39 (s, 3H), 6.04 (d, 1H, $^3J_{H-H}$=2.8), 6.69 (s, 1H), 6.73 (s, 1H), 6.98 (d, 1H, $^3J_{H-H}$=2.7). $^{13}$C{$^1$H} NMR (C$_6$D$_6$): δ 2.01, 4.15, 34.50, 52.35, 55.20, 55.47, 58.22, 90.95, 103.27, 105.38, 113.49, 125.14, 128.90, 129.07, 152.14, 153.09.

EXAMPLE 15

Step 1 Preparation of 5,6-Dimethoxy-3-phenyl-1H-indene

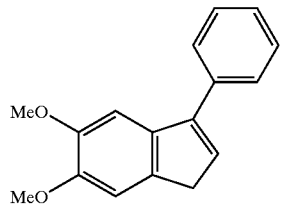

2,3-Dihydro-5,6-dimethoxy-3-phenyl-1H-inden-1-one (8.010 g, 29.85 mmol) and NaBH$_4$ (1.355 g, 35.82 mmol) were stirred in diethylether (100 mL) at 0° C. as ethanol (100 mL) was added slowly. The mixture was allowed to stir at room temperature for 24 hours. The mixture was then poured onto crushed ice and then washed with diethylether (3×100 mL). The organic fractions were then dried over MgSO$_4$, filtered, and the volatile components were removed under vacuum resulting in the isolation of a yellow solid. This solid was refluxed in anhydrous DMSO (150 mL) for 5 hours and then cooled to room temperature. The mixture was poured onto crushed ice and the total volume was diluted to 500 mL using H$_2$O. This mixture was then washed using diethylether (5×100 mL). The organic fractions were then combined, washed with H$_2$O (1×100 mL) and then dried over MgSO$_4$. The mixture was filtered and the volatile components were removed resulting in the isolation of a dark red oil. Chromatography of the oil on silica gel using hexane/CH$_2$Cl$_2$ (1/1 vol) as the diluent resulted in the isolation of the 5,6-dimethoxy-3-phenyl-1H-indene as a yellow microcrystalline solid (4.91 g, 65.2 percent yield).

$^1$H NMR (C$_6$D$_6$): δ 3.17 (s, 2H), 3.43 (s, 3H), 3.53 (s, 3H), 6.3 (m, 1H), 6.88 (s, 1H), 7.1–7.1 (m, 1H), 7.22 (s, 1H), 7.29 (t, $^3J_{H-H}$=7.2 Hz, 2H), 7.63 (d, $^3J_{H-H}$=7.4 Hz, 2H). $^{13}$C{$^1$H} NMR (C$_6$D$_6$): δ 38.18, 55.98, 56.13, 105.61, 109.59, 127.69, 128.97, 129.46, 137.19, 137.66, 145.79, 148.94, 149.60.

Step 2 Preparation of (5,6-Dimethoxy-3-phenyl-1H-inden-1-yl)lithium.

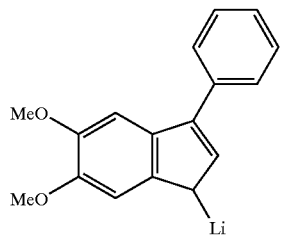

5,6-dimethoxy-3-phenyl-1H-indene (1.26 g, 4.99 mmol) was dissolved in a mixture of 15 mL of toluene and 25 mL of hexane and 3.06 mL of 1.6 M n-BuLi were added dropwise via syringe over a 3 min period. The solution developed a yellow-light green precipitate during addition of n-BuLi. The reaction mixture was stirred for 3 h and then filtered, washed with 60 mL of hexane and dried in vacuum to afford the desired product as a yellow solid (1.24 g) in 98 percent yield.

Step 3 Preparation of 1-(5,6-Dimethoxy-3-phenyl-1H-inden-1-yl)-N-(1,1-dimethylethyl)-1,1-dimethylsilanamine

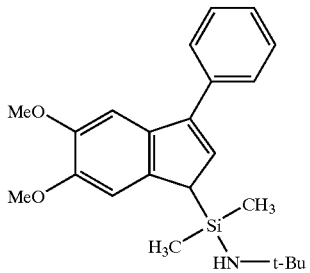

(5,6-dimethoxy-3-phenyl-1H-inden-1-yl)lithium (1.24 g, 4.8 mmol) was dissolved in 20 mL of THF and added to a solution of N-(tert-butyl)-N-(1-chloro-1,1-dimethylsilyl)amine (1.035 g, 6.24 mmol) in 50 mL of THF over a 25 min period, with stirring continued for 20 h. The solution was then evaporated under reduced pressure and the residue was extracted with hexane (50 mL). After filtration, the solvent was removed under reduced pressure. To this residue, 30 mL of hexane was added and the flask was put aside into a freezer (−27° C.) for 2 days. After that time the crystallized solid was filtered off and the solvent was removed leaving 1.68 of the product as a yellow oil.

Step 4 Preparation of (1-(((1,1-Dimethylethyl)amino)dimethylsilyl)-5,6-dimethoxy-3-phenyl-1H-inden-1-yl)lithium, Lithium Salt.

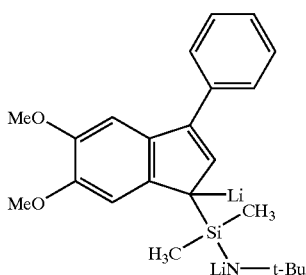

1.68 g (4.4 mmol) of 1-(5,6-dimethoxy-3-phenyl-1H-inden-1-yl)-N-(1,1-dimethylethyl)-1,1-dimethylsilanamine were combined with 50 mL of hexane. To this solution, 5.5 mL (8.8 mmol) of n-BuLi (1.6 M) were added dropwise resulting in immediate formation of a precipitate. After stirring for 7 h at room temperature, the resulting precipitate was collected via filtration, washed with 40 mL of hexane and then dried under reduced pressure to give 1.71 g of the product as a yellow solid. Yield was 99 percent.

Step 5 Preparation of Dichloro(1-((1,2,3,3a,7a-η)-5,6-dimethoxy-3-phenyl-1H-inden-1-yl)-N-(1,1-dimethylethyl)-1,1-dimethylsilanaminato(2-)-N)titanium.

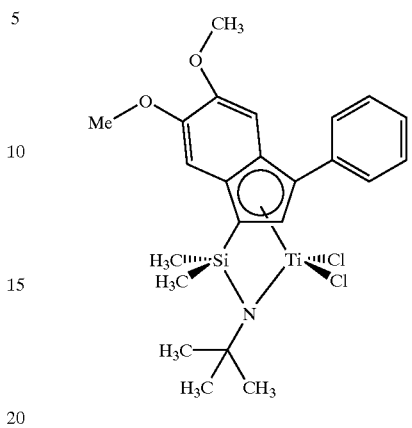

1.61 g (4.4 mmol) Of TiCl$_3$·(THF)$_3$ were suspended in 40 mL of THF. To this solution, 1.71 g (4.4 mmol) of (1-(((1,1-dimethylethyl)amino)dimethylsilyl)-5,6-dimethoxy-3-phenyl-1H-inden-1-yl)lithium, lithium salt dissolved in 30 mL of THF were added within 5 min. The solution was then stirred for 50 minutes, after which 0.79 g of PbCl$_2$ (2.8 mmol) were added. After stirring for an additional 50 minutes, THF was removed under reduced pressure. The residue was dissolved in 50 mL of toluene and the solution was filtered. Toluene was removed under reduced pressure leaving a red solid. The product was recrystallized from warm hexane and dried under reduced pressure to give 0.367 g, 17 percent, of highly pure product.

$^1$H NMR (CD$_2$Cl$_2$) δ 0.51 (s, 3H), 0.69 (s, 3H), 1.39 (s, 9H), 3.28 (s, 3H), 3.33 (s, 3H), 6.59 (s, 1H), 6.87 (s, 1H), 7.08 (s, 1H), 7.16 (t, 1H, $^3J_{H-H}$=7.7 Hz), 7.29 (t, 2H), $^3J_{H-H}$=7.4 Hz), 7.74 (d, 2H, $^3J_{H-H}$=7.5 Hz). $^{13}$C{$^1$H} NMR (CD$_2$Cl$_2$) δ 0.96, 3.58, 32.64, 55.28, 55.39, 62.59, 97.82, 101.94, 105.37, 124.90, 128.72, 128.97, 129.35, 131.05, 132.67, 135.22, 135.88, 153.93, 155.67.

EXAMPLE 16

Preparation of (1-((1,2,3,3a,7a-η)-5,6-Dimethoxy-3-phenyl-1H-inden-1-yl)-N-(1,1-dimethylethyl)-1,1-dimethylsilanaminato(2-)-N)dimethyltitanium

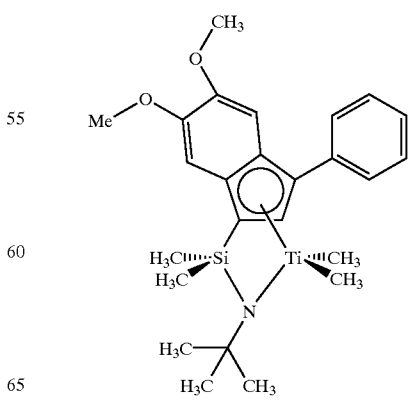

Dichloro(1-((1,2,3,3a,7a-η)-5,6-dimethoxy-3-phenyl-1H-inden-1-yl)-N-(1,1-dimethylethyl)-1,1-dimethylsilanaminato(2-)-N)titanium (0.107 g, 0.210 mmol) was stirred in diethylether (50 mL) while MeMgBr (0.430 mmol, 0.306 mL of 3.0 M solution in diethylether) was added dropwise. This mixture was then allowed to stir for 30 minutes. After the reaction period the volatiles were removed and the residue was extracted and filtered using hexane. Removal of the hexane under vacuum resulted in the isolation of the desired product as a yellow residue which solidified upon standing. Yield was 0.031 g, 31.7 percent.

$^1$H NMR (C$_6$D$_6$): δ 0.19 (s, 3H), 0.49 (s, 3H), 0.66 (s, 3H), 0.71 (s, 3H), 1.51 (s, 9H), 3.34 (s, 3H), 3.36 (s, 3H), 6.35 (s, 1H), 6.81 (s, 1H), 7.1–7.4 (m, 3H), 7.30 (s, 1H), 7.74 (d, $^3J_{H-H}$=7.4 Hz, 2H). $^{13}$C{$^1$H} NMR (C$_6$D$_6$): δ 1.92, 4.29, 34.54, 54.68, 55.18, 55.31, 57.74, 58.66, 91.99, 101.95, 105.75, 122.80, 127.05, 127.37, 129.09, 130.30, 136.96, 151.83, 153.52.

Polymerizations

A two-liter Parr reactor was charged with 740 g of Isopar-E™ mixed alkanes solvent (available from Exxon Chemicals Inc.) and 118 g of 1-octene comonomer. Hydrogen was added as a molecular weight control agent by differential pressure expansion from a 75 mL addition tank at 25 psi (2070 kPa). The reactor was heated to the polymerization temperature of 140° C. and saturated with ethylene at 500 psig (3.4 MPa). The appropriate amount of catalyst and cocatalyst as 0.005M solutions in toluene were premixed in the drybox. After the desired premix time, the solution was transferred to a catalyst addition tank and injected into the reactor. The polymerization conditions were maintained for 15 minutes with ethylene on demand. The resulting solution was removed from the reactor, and a hindered phenol antioxidant (Irganox™ 1010 from Ciba Geigy Corporation) was added. Polymers formed were dried in a vacuum oven set at 120° C. for about 20 hours. Results are in Table 1.

TABLE 1

| run | catalyst | Density[a] | Mi[b] | Efficiency[c] |
|---|---|---|---|---|
| 1* | A | 0.895 | 5 | 1.3 |
| 2 | B | 0.905 | 0.04 | 1.1 |
| 3 | C | 0.914 | 0.04 | 1.0 |
| 4 | D | 0.925 | 0.889 | 0.4 |

*comparative, not an example of the invention
A (N-(1,1-dimethylethyl)-1,1-dimethyl-1-[(1,2,3,4,5-η)-2,3,4,5-tetramethyl-2-4-cyclopentadien-1-yl]silanaminato(2-)-N]dimethyltitanium
B N-(1,1-dimethylethyl)-1-((1,2,3,3a,7a-η)-5-methoxy-3-(1-pyrrolidinyl)-1H-inden-1-yl)-1,1-dimethylsilanaminato(2-)-N)dimethyltitanium (Example 2)
C (1-((1,2,3,3a,7a-η)-5,6-dimethoxy-3-(1-pyrrolidinyl)-1H-inden-1-yl)-N-(1,1-dimethylethyl)-1,1-dimethylsilanaminato(2-)-N)dimethyltitanium (Example 8)
D (N-(1,1-dimethylethyl)-1,1-dimethyl-5-((4a,5,6,7,7a-η)-6-methyl-5H-indeno(5,6-d)-1,3-dioxol-5-yl)silanaminato(2-)-N)dimethyititanium (Example 10)
[a]g/cm$^3$
[b]melt index, determined by micromelt technique, dg/min
[c]catalyst efficiency, g polymer/μg Ti

What is claimed is:

1. A metal complexes corresponding to the formula:

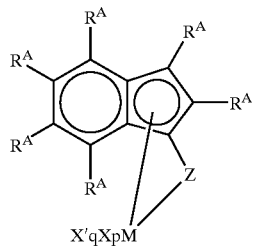

I where M is a metal from Group 4 of the Periodic Table of the Elements which is in the +2, +3 or +4 formal oxidation state, $R^A$ independently each occurrence is hydrogen, $R^B$ or $TR^B{}_j$, with the proviso that in at least two but not more than three occurrences $R^A$ is $TR^B{}_j$, j is 1 or 2, and when j is 1, T is oxygen or sulfur and when j is 2, T is nitrogen or phosphorus, $R^B$ independently each occurrence is a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, or two $R^B$ groups are joined together forming a divalent ligand group;

Z is a divalent moiety bound to the substituted indenyl group and bound to M by either covalent or coordinate covalent bonds, comprising boron or a member of Group 14 of the Periodic Table of the Elements, and also comprising nitrogen, phosphorus, sulfur or oxygen;

X is an anionic or dianionic ligand group having up to 60 atoms including ligands that are cyclic, delocalized, π-bound ligand groups;

X' independently each occurrence is a Lewis base ligand having up to 20 atoms;

p is a number from 0 to 5, when each X is an anionic ligand, p is two less than the formal oxidation state of M, when some or all X groups are dianionic ligand groups each dianionic X group accounts for two valencies and p is correspondingly reduced in value; and q is zero, 1 or 2.

2. The metal complex of claim 1, corresponding to the formula:

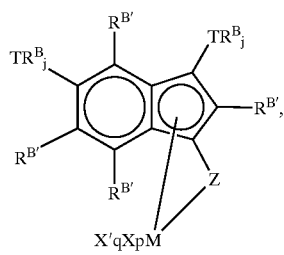

II

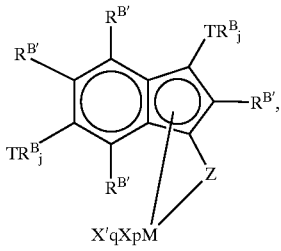

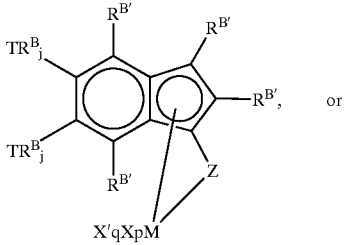

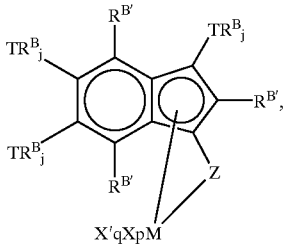

where T, $R^B$, j, M, Z, X, X', p and q are as previously defined in claim 1, and $R^{B'}$ independently is hydrogen or a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, or two $R^{B'}$ groups are joined together forming a divalent ligand group.

3. The metal complex of claim 2 corresponding to the formula:

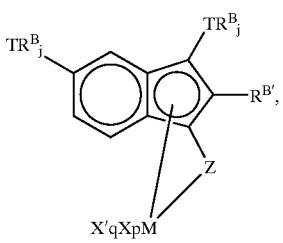

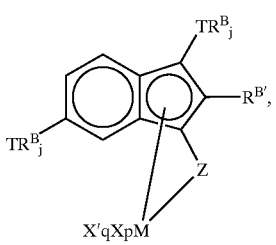

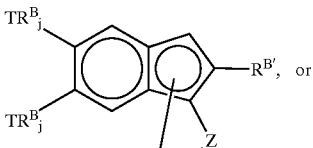

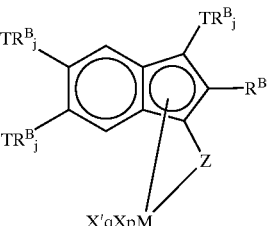

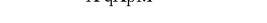

where Z, T, $R^B$, $R^{B'}$, j, M, X, X', p and q are as previously defined with respect to formulas II, III IV and V.

4. The metal complex of claim 3 wherein where —Z— is —(Z*—Y)—, with Z* bonded to the cyclopentadienyl moiety and Y bonded to M, and Y is —O—, —S—, —NR*—, —NR*$_2$, —PR*—, —PR*$_2$, —OR*, or —SR*;

Z* is SiR*$_2$, CR*$_2$, SiR*$_2$SiR*$_2$, CR*$_2$CR*$_2$, CR*=CR*, CR*$_2$SiR*$_2$, CR*$_2$SiR*$_2$CR*$_2$, SiR*$_2$CR*$_2$SiR*$_2$, CR*$_2$CR*$_2$SiR*$_2$, CR*$_2$CR*$_2$CR*$_2$, or GeR*$_2$; and R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms, and optionally, two R* groups from Z, or an R* group from Z and an R* group from Y form a ring system;

p is 2, q is zero, M is in the +3 or +4 formal oxidation state, and X is independently each occurrence chloride, methyl, benzyl, trimethylsilylmethyl, allyl, cyclopentadienyl, pyrollyl or two X groups together are 1,4-butane-diyl, 2-butene-1,4-diyl, 2,3-dimethyl-2-butene-1,4-diyl, 2-methyl-2-butene-1,4-diyl, or xylanediyl.

5. The complex of claim 4 wherein Z* is SiR$_2$* and Y is —NR*—.

6. The complex of claim 1 wherein M is titanium.

7. A catalyst composition for olefin polymerization comprising in combination:

(A) a catalyst component comprising a metal complex of any one of claims 1–6 and (B) a cocatalyst component comprising an activating cocatalyst wherein the molar ratio of (A) to (B) is from 1:10,000 to 100:1.

8. A process for polymerizing olefins comprising contacting one or more $C_{2-20}$ α-olefins under polymerization conditions with a catalyst composition of claim 7.

* * * * *